（12）# United States Patent
Blumenthal

(10) Patent No.: US 10,952,710 B2
(45) Date of Patent: Mar. 23, 2021

(54) BALLOON CLOSURE DEVICE

(71) Applicant: Steven Jay Blumenthal, Cold Spring Harbor, NY (US)

(72) Inventor: Steven Jay Blumenthal, Cold Spring Harbor, NY (US)

( * ) Notice: Subject to any disclaimer, the term of this patent is extended or adjusted under 35 U.S.C. 154(b) by 0 days.

(21) Appl. No.: 16/031,141

(22) Filed: Jul. 10, 2018

(65) Prior Publication Data

US 2019/0015086 A1 Jan. 17, 2019

Related U.S. Application Data

(60) Provisional application No. 62/533,054, filed on Jul. 16, 2017.

(51) Int. Cl.
*A61B 17/00* (2006.01)
*A61B 90/00* (2016.01)

(52) U.S. Cl.
CPC .......... *A61B 17/0057* (2013.01); *A61B 90/08* (2016.02); *A61B 2017/0061* (2013.01); *A61B 2017/00336* (2013.01); *A61B 2017/00557* (2013.01); *A61B 2017/00623* (2013.01); *A61B 2017/00654* (2013.01); *A61B 2017/00672* (2013.01); *A61B 2017/00676* (2013.01); *A61B 2017/00884* (2013.01); *A61B 2090/0811* (2016.02)

(58) Field of Classification Search
CPC ............ A61B 17/0057; A61B 17/0467; A61B 2017/00557; A61B 2017/00654; A61B 2017/00659
See application file for complete search history.

(56) References Cited

U.S. PATENT DOCUMENTS

| 5,108,421 | A | | 4/1992 | Fowler | |
|---|---|---|---|---|---|
| 5,192,302 | A | | 3/1993 | Kensey et al. | |
| 5,222,974 | A | | 6/1993 | Kenset et al. | |
| 5,413,571 | A | * | 5/1995 | Katsaros | A61B 17/0057 128/899 |
| 6,048,358 | A | * | 4/2000 | Barak | A61B 17/0057 606/213 |
| 6,071,300 | A | * | 6/2000 | Brenneman | A61B 17/0057 604/265 |
| 6,139,556 | A | * | 10/2000 | Kontos | A61B 17/0057 606/144 |
| 6,296,657 | B1 | * | 10/2001 | Brucker | A61B 17/0057 606/192 |

(Continued)

*Primary Examiner* — Julie A Szpira

(57) ABSTRACT

A system is provided for causing hemostasis at a puncture and a puncture tract. The system includes an inner member comprising an expandable member at its distal end and an inflation lumen that extends from inner member proximal end to an interior of the expandable member. The system further includes an outer member comprising a lumen sized and shaped to allow the inner member to slide therein, an occlusion balloon at its distal end, and an inflation lumen that extends from its proximal end to the interior of the occlusion balloon. The expandable member can be inflated by fluid flowing through the inner member inflation lumen so that the expandable member can close a puncture in a subcutaneous vessel of a living being. The occlusion balloon can be inflated by fluid flowing through the outer member inflation lumen so that the occlusion balloon can contact and apply pressure to a puncture tract extending from the skin of the living being to the puncture.

23 Claims, 26 Drawing Sheets

(56) References Cited

U.S. PATENT DOCUMENTS

| | | | |
|---|---|---|---|
| 6,371,975 B2* | 4/2002 | Cruise | A61B 17/00491 606/214 |
| 7,025,776 B1* | 4/2006 | Houser | A61B 17/0057 606/213 |
| 7,331,979 B2 | 2/2008 | Khosravi et al. | |
| 7,789,893 B2* | 9/2010 | Drasler | A61B 17/0057 606/213 |
| 8,444,671 B2* | 5/2013 | Yassinzadeh | A61B 17/0057 606/213 |
| 2002/0072767 A1* | 6/2002 | Zhu | A61B 17/0057 606/213 |
| 2002/0133123 A1* | 9/2002 | Zucker | A61B 17/0057 604/246 |
| 2003/0055397 A1* | 3/2003 | Zucker | A61B 17/0057 604/509 |
| 2003/0125766 A1* | 7/2003 | Ding | A61B 17/0057 606/213 |
| 2004/0153060 A1* | 8/2004 | Lindenbaum | A61B 17/0057 606/49 |
| 2008/0065150 A1* | 3/2008 | Drasler | A61B 17/0057 606/213 |
| 2008/0154303 A1* | 6/2008 | Yassinzadeh | A61B 17/0057 606/213 |
| 2011/0106148 A1* | 5/2011 | Ginn | A61B 17/0057 606/213 |

\* cited by examiner

BALLOON CLOSURE DEVICE

FIELD OF THE INVENTION

The present invention relates generally to a system and methods for sealing punctures in a body, and more particularly, to a system and methods for sealing a percutaneous puncture extending from a patient's skin through tissue into a blood vessel or other body lumen.

BACKGROUND OF THE INVENTION

A system and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various systems and methods have been suggested for sealing a percutaneous puncture instead of using external pressure. For example, U.S. Pat. No. 5,108,421 to Fowler discloses a collagen plug that may be delivered into a puncture through tissue. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon, thereby preventing the plug from entering the vessel. Once the plug is positioned within the puncture, the balloon may be deflated and withdrawn, leaving the plug therein to expand and seal the puncture and/or to promote hemostasis.

Alternatively, U.S. Pat. Nos. 5,192,302 and 5,222,974 issued to Kensey et al. describe a biodegradable collagen plug and rigid anchor that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism. In addition, the disclosed plug may not completely occlude the puncture site, resulting in incomplete hemostasis and vascular complications.

U.S. Pat. No. 7,331,979 issue to Khosravi et al. describes a balloon that may be delivered through an introducer sheath into a puncture site. The balloon is withdrawn to seal the puncture, and a hydrogel sealant is introduced into the puncture. The balloon is then removed, relying on the hydrogel sealant to occlude the tissue tract. The sealant may not completely occlude the puncture site or tissue tract, resulting in incomplete hemostasis and vascular complications.

Accordingly, the present invention's system and methods for sealing punctures may have multiple advantages. Similarly, to assessing hemostasis with manual compression, the occlusion balloon may be deflated to assess hemostasis, and reinflated until hemostasis has been confirmed. When other devices, as noted above, fail to achieve hemostasis, the only option is manual compression. With the present invention, prolonged balloon inflation is localized to the puncture tract with nothing intravacular to impair blood flow, does not require additional manpower or beyond standard supervision, may not be uncomfortable for the patient, and it may be possible for the patient to move or even ambulate with the device inflated and secured in the tissue tract. In addition, the device may be scalable for larger punctures, which may require more prolonged and possibly overnight balloon inflation to achieve hemostasis.

SUMMARY OF THE INVENTION

The present invention is directed to a system and methods for sealing a puncture in a body, and, more particularly, to a system and methods for providing temporary or permanent hemostasis within a percutaneous puncture comprising a tract extending from a patient's skin, through tissue, to a blood vessel or other body lumen.

In accordance with the present invention, a system is provided for sealing a puncture through tissue that includes an outer member, an inner member slidably coupled to the outer member, and balloons or other expandable members separately coupled to the distal ends of both the inner and outer members. The inner member also includes a vessel locator.

In one embodiment, the outer member may include proximal and distal ends defining a longitudinal axis therebetween, a lumen extending between the proximal and distal ends to accommodate the inner member, and an inflation lumen extending between the proximal and distal ends. The expandable member may be coupled circumferentially to the outer border of a distal end segment of the outer member such that an interior of the expandable member communicates with the inflation lumen. Thus, the expandable member may be expandable from a collapsed state to an expanded state when fluid is introduced into the inflation lumen of the outer member, and consequently into the interior of the expandable member.

The inner member may include proximal and distal ends, and an inflation lumen extending between the proximal and distal ends. The inner member is slidably disposed within the lumen of the outer member. The expandable member may be coupled circumferentially to the outer border of a distal end segment of the inner member such that an interior of the expandable member communicates with the inflation lumen. Similarly, the expandable member may be expandable from a collapsed state to an expanded state when fluid is introduced into the inflation lumen of the inner member, and consequently into the interior of the expandable member.

In one embodiment, the outer member may connect to a hemostatic valve on its proximal end, through which the inner member may pass. Such hemostatic valve may be self-closing or manually closed to essentially lock the outer and inner members together allowing them to move as a unit, or restricting their joint movement as desired.

The outer member may include a port on the proximal end that communicates with the inflation lumen, i.e., for connecting a source of fluid to the lumen. The expandable member, coupled with the outer member, may be expanded, i.e., as fluid is delivered into the lumen, and may be collapsed, i.e., as fluid is withdrawn from the lumen, as may be seen with a balloon. Similarly, the inner member may include a port on the proximal end that communicates with the inflation lumen, i.e., for connecting a source of fluid to the lumen. The expandable member, coupled with the inner member, may be expanded, i.e., as fluid is delivered into the lumen, and may be collapsed, i.e., as fluid is withdrawn from the lumen, as may be seen with a balloon.

The system may be referred to as the balloon closure device, the outer member may be referred to as the occlusion catheter, the expandable member coupled to the outer member may be referred to as the occlusion balloon, the inner member may be referred to as the anchor catheter, and the expandable member coupled to the inner member may be referred to as the anchor balloon. The anchor catheter may also include a vessel locator at its distal end.

In accordance with an embodiment, a method is provided for sealing a puncture extending through tissue and/or communicating with a body lumen using a system including an occlusion catheter, an anchor/introducer catheter slidably coupled to the occlusion catheter, an occlusion balloon coupled to the distal end of the occlusion catheter, an anchor balloon coupled to the distal end of the anchor catheter, and a vessel locator at the distal end of the anchor catheter. This design may avoid the need for a separate introducer sheath, as the anchor catheter may act as the introducer for the occlusion catheter. For example, the body lumen may be a blood vessel, e.g., a femoral, carotid, or other peripheral artery.

The balloon closure device, e.g., an anchor catheter, and occlusion catheter, is arranged for location within a portion of the puncture at a desired position with respect thereto, e.g., the anchor catheter within the vessel and the occlusion catheter within the puncture/tissue tract, to enable the effective sealing of the puncture by the closure device. The vessel locator, built into the distal end of the anchor catheter, is arranged for introduction into the puncture to locate the wall of the blood vessel and basically comprises means for extension of the anchor catheter in the puncture tract to a position whereupon blood within the vessel is enabled to flow from the interior of the vessel into the vessel locator for detection thereof.

There may be various possible methods for delivering the balloon closure device into the puncture tract, across the puncture, and into the body lumen, as desired. Optionally, the system may include an elongate tubular member, e.g., an introducer sheath, including proximal and distal ends, and a lumen extending therebetween. The lumen may have sufficient size for receiving the outer member therein when the expandable member is in the collapsed state. In this embodiment, the introducer sheath may be a valved hemostatic peel-away sheath. Using this technique, the existing sheath is exchanged for the peel-away sheath, using techniques known in the art. Whereupon, the balloon closure device may be delivered through the sheath to the desired destination. This method requires a peel-away sheath closely corresponding to the size of the existing sheath.

The balloon closure device may be delivered in fewer steps by designing the anchor catheter to also function as the introducer. In this embodiment, the occlusion catheter lumen may have sufficient size for receiving the anchor catheter/introducer. The anchor catheter/introducer may be advanced distal to the occlusion catheter, and then the two may be secured together using the above mentioned hemostatic valve, allowing the two to be advanced as a unit. Tracking over a guidewire, an adequately stiff and tapered anchor catheter/introducer should be able to easily traverse the puncture tract, and enter the body lumen, with the tethered occlusion catheter advanced to the distal end of the puncture tract. This is similar to advancing a vascular sheath with its introducer, as is known in the art. In the case of a blood vessel or other fluid-filled lumen, the anchor catheter/introducer may have a method, e.g., a vessel locator, to indicate that it has entered the lumen. The anchor catheter may, alternatively, enter the lumen simply by being advanced an adequate distance through the puncture tract, based on the original sheath length.

The above mentioned embodiment, with the anchor catheter nested within the occlusion catheter, may result in a balloon closure device with a larger profile. This may not be an issue when using the device to occlude large diameter puncture holes. However, to occlude smaller diameter puncture holes, it may be preferable to use a tapered dilator/introducer rather than the aforementioned anchor catheter, to be nested within the occlusion catheter. This alternative embodiment may result in a smaller profile device. Such a dilator/introducer may similarly have a distal vessel locator to indicate entry into the blood vessel lumen, but would lack an anchor balloon. Instead, the guide wire may be removed and a simple balloon catheter, as is known in the art, may be advanced through the guide wire lumen, enter the blood vessel and function similarly to the anchor balloon, to be further described below.

Any of the aforementioned embodiments may be used to deliver the balloon closure device with similar subsequent steps as described below. The balloon closure device may be introduced into the puncture with the occlusion and anchor balloons in a collapsed state until the expandable member is disposed within the body lumen. If necessary, for example, the system may be introduced through a lumen of a peel-away introducer sheath or other tubular member previously placed in the puncture. In either embodiment, the anchor catheter may be advanced more distally than the occlusion catheter, to enter the body lumen. Once, intraluminal position is confirmed, fluid may be introduced into the anchor catheter to expand the coupled anchor balloon to an expanded state. The anchor catheter may be at least partially withdrawn from the puncture until the anchor balloon engages tissue at a location where the puncture penetrates a wall of the body lumen, thereby substantially sealing the puncture from the body lumen. While pull-back tension is applied to the anchor balloon that is "anchored" in the body lumen, the occlusion catheter may be advanced distally until it abuts the anchor balloon. The introducer sheath, if required, may be retracted, peeled away, and removed. The occlusion balloon may be expanded against the puncture tract wall while also engaging the tissue contiguous with the puncture on the opposite side thereof from the anchor balloon, effectively occluding the puncture, and puncture tract and preventing dislodgment of the balloon closure device. Next, the anchor balloon may be collapsed, withdrawn from the body lumen through the puncture, withdrawn from the puncture tract, and completely removed. The occlusion balloon is designed to completely seal the puncture and the puncture tract. At this point, the balloon closure device is completely outside the body lumen, with the expanded occlusion balloon adhering to the tissue contiguous with the puncture and the puncture tract, essentially locking the balloon closure device in the puncture tract. Optionally, the occlusion balloon may be coated with a procoagulant material (e.g., Chitosan) to enhance coagulation and hemostasis. A transparent adhesive dressing (e.g., Tegaderm) may be applied to further secure the balloon closure device in place.

After an appropriate time interval, depending on the size and nature of the puncture (e.g., artery vs. vein), the occlusion balloon may be collapsed, and an assessment of hemostasis may be made, with the patient both at rest and with ambulation. Once hemostasis is confirmed, the balloon closure device may be completely removed from the puncture tract. After adequate balloon occlusion, there should be no need for any manual compression.

Other objects and features and many of the attendant advantages of the present invention will become apparent from consideration of the following detailed description taken in conjunction with the accompanying drawings.

DETAILED DESCRIPTION OF THE PREFERRED EMBODIMENTS

Figure 1:
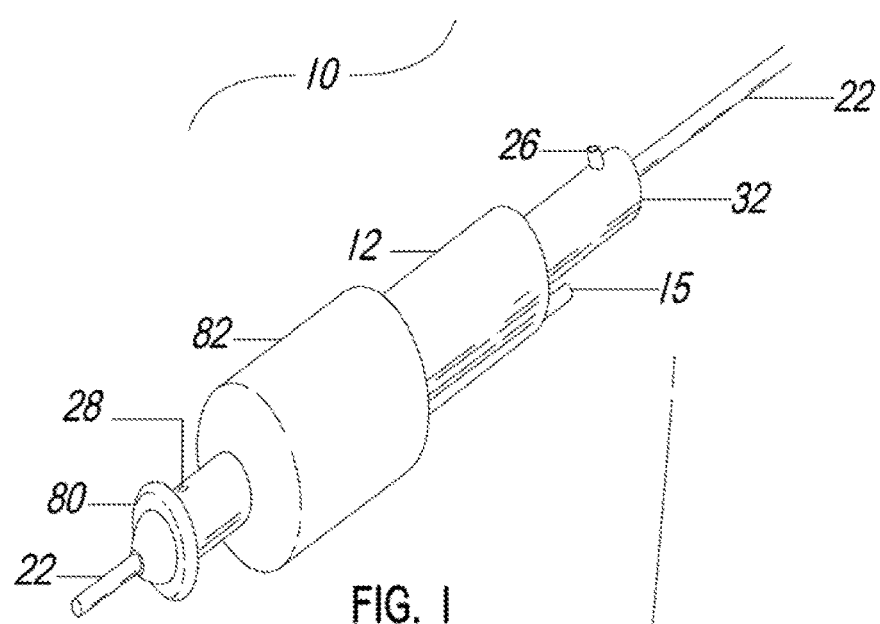
FIG. 1 is a perspective view of an embodiment of a system for sealing a puncture through tissue, in accordance with the present invention.

Referring now in greater detail to the various figures of the drawings wherein like reference characters refer to like parts. Turning to the drawings, FIGS. 1-12, show an embodiment of the system, referred to as the balloon closure device 10 for sealing a puncture extending through tissue and/or communicating with a body lumen. The puncture 190 includes not only the opening in the wall of the vessel but also the puncture tract 190A, i.e., the passageway in the tissue located between the vessel and the skin of the being formed when the vessel is punctured.

Figure 2:
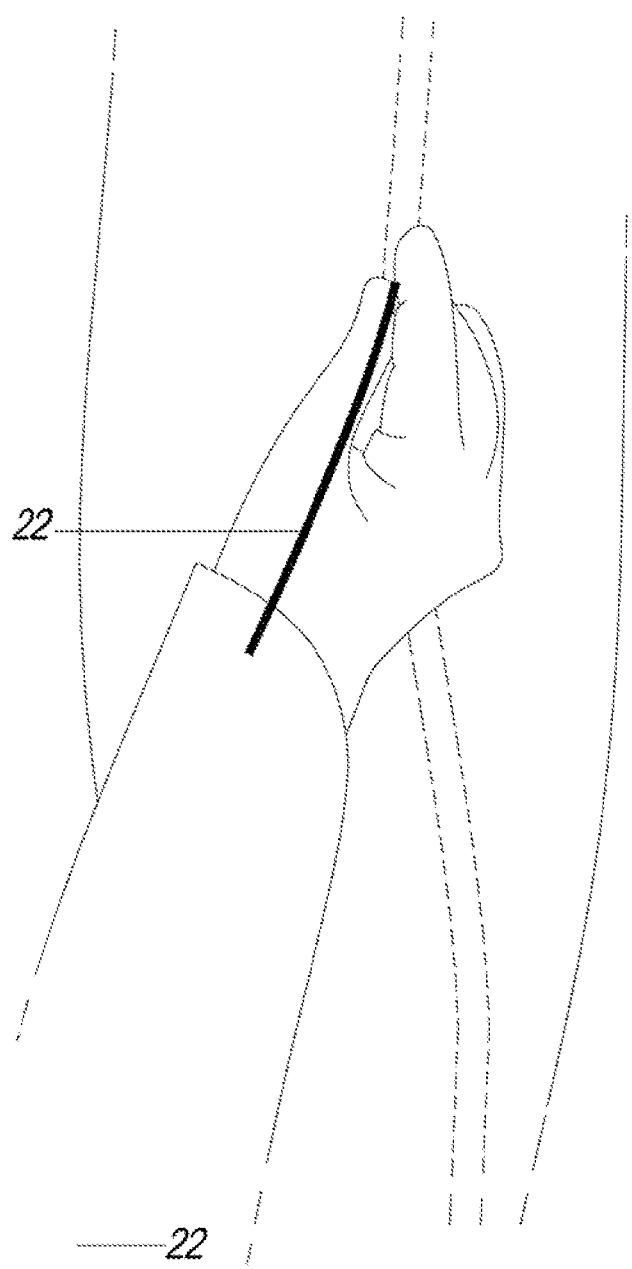
FIG. 2 is a perspective view, showing an operator inserting a guide wire into a patient's blood vessel.
Figure 3:
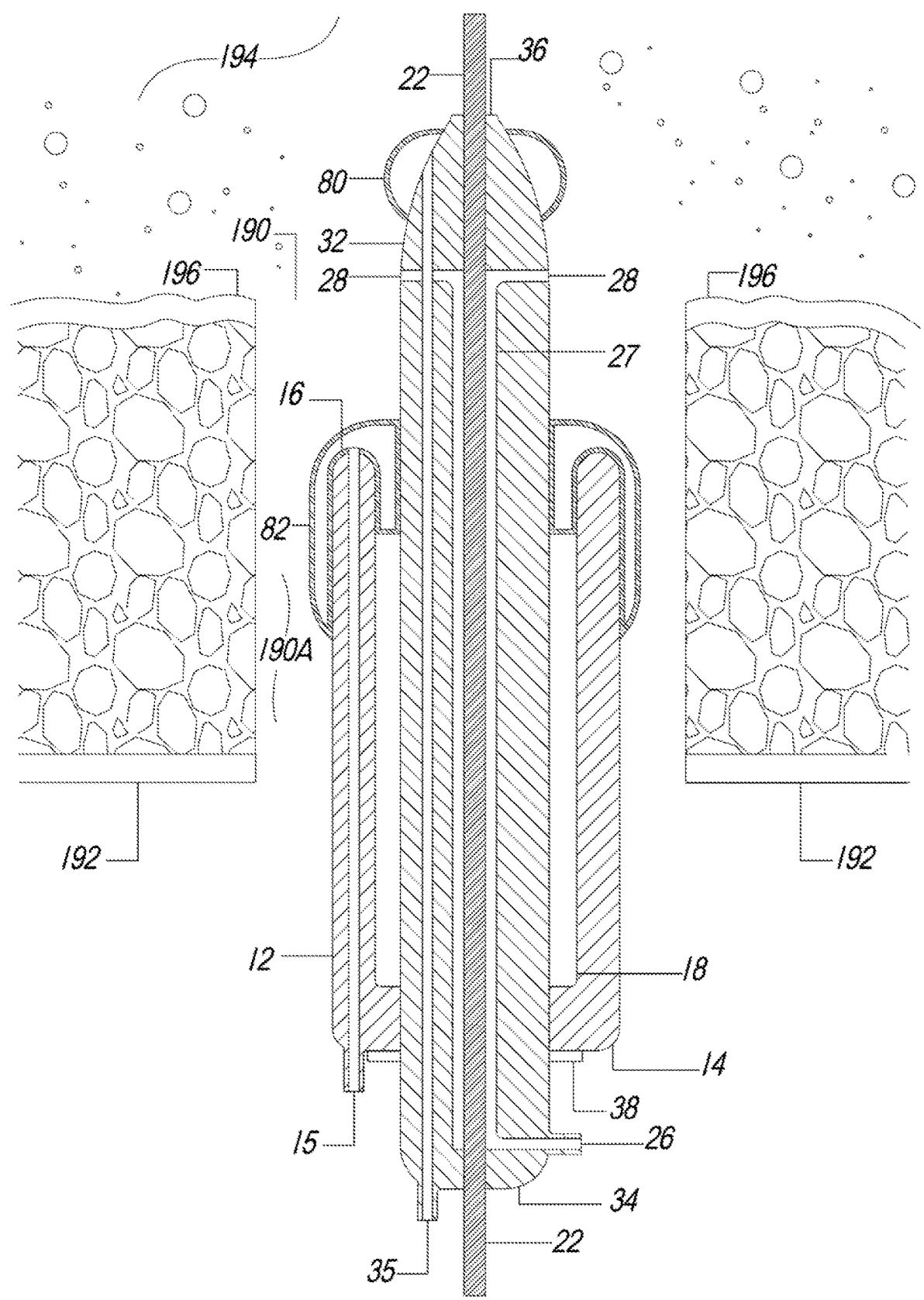
FIG. 3 is a schematic sectional representation of an embodiment of a system for sealing a puncture through tissue, in accordance with the present invention.
Figure 4:
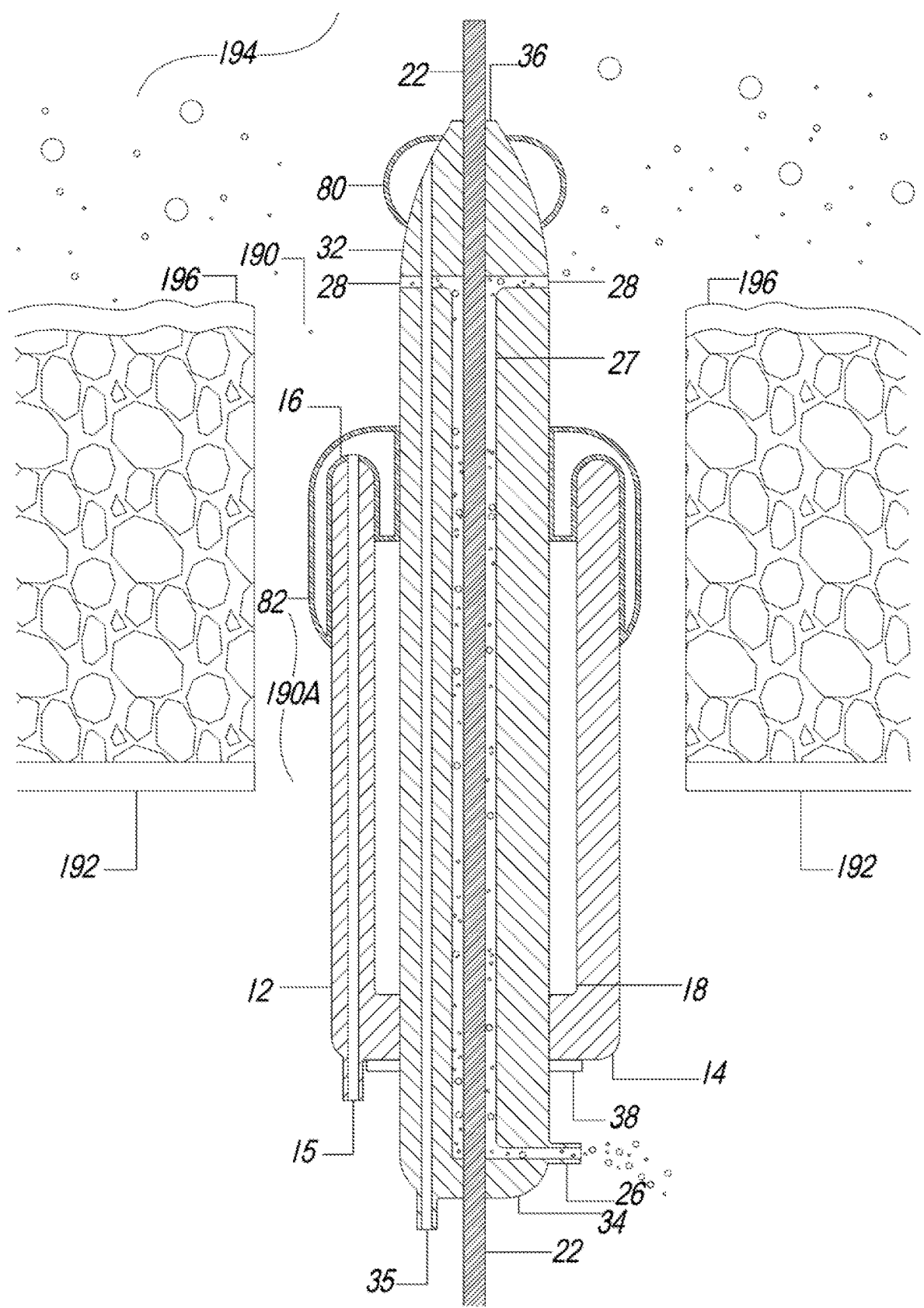
FIG. 4 is a schematic sectional representation of the embodiment of FIG. 3 in use and showing blood flow from the arterial lumen.
Figure 5:
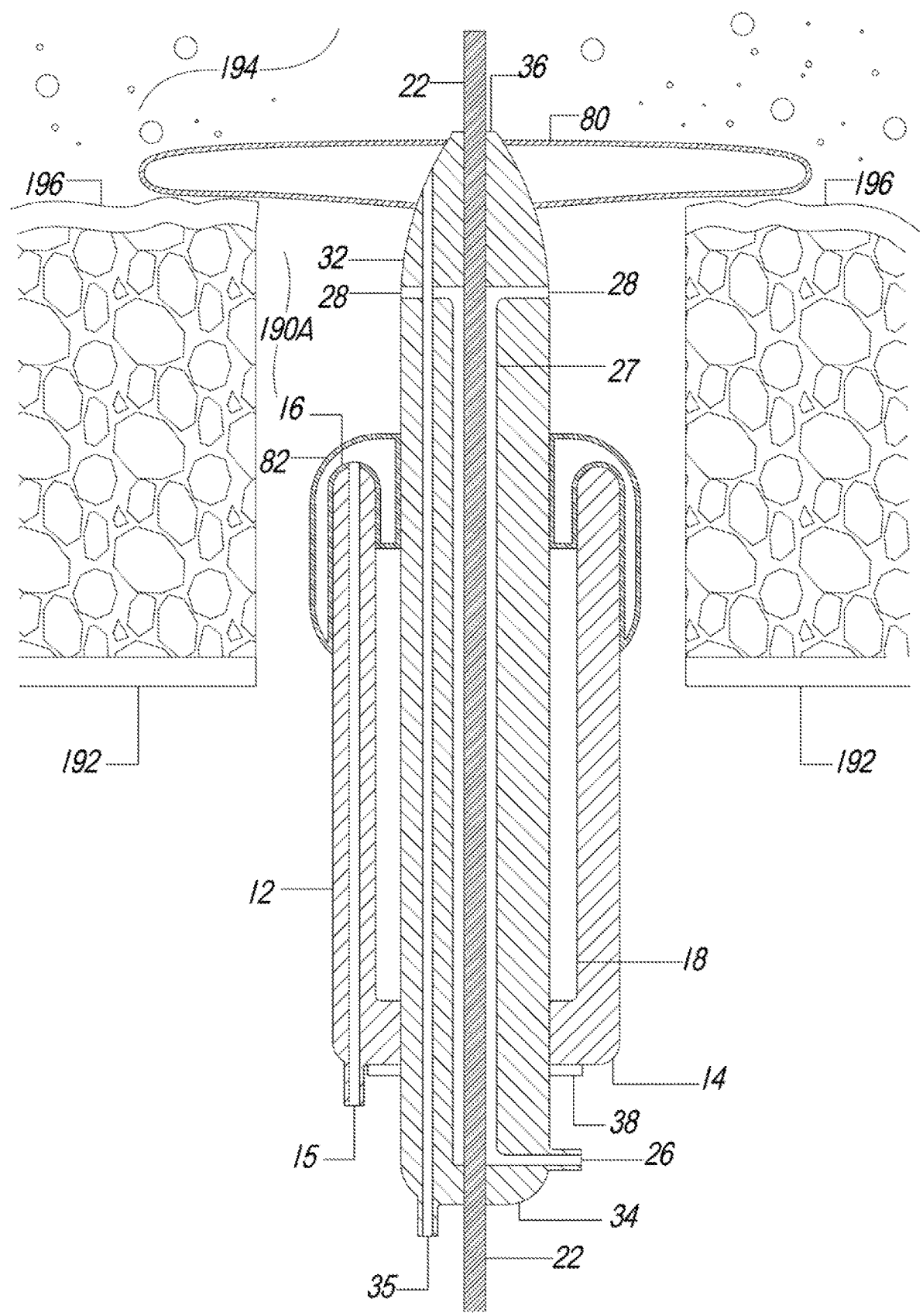
FIG. 5 is a schematic sectional representation of the embodiment of FIG. 3 in use showing an anchor balloon inflated and an anchor catheter/introducer occluding a puncture.
Figure 6:
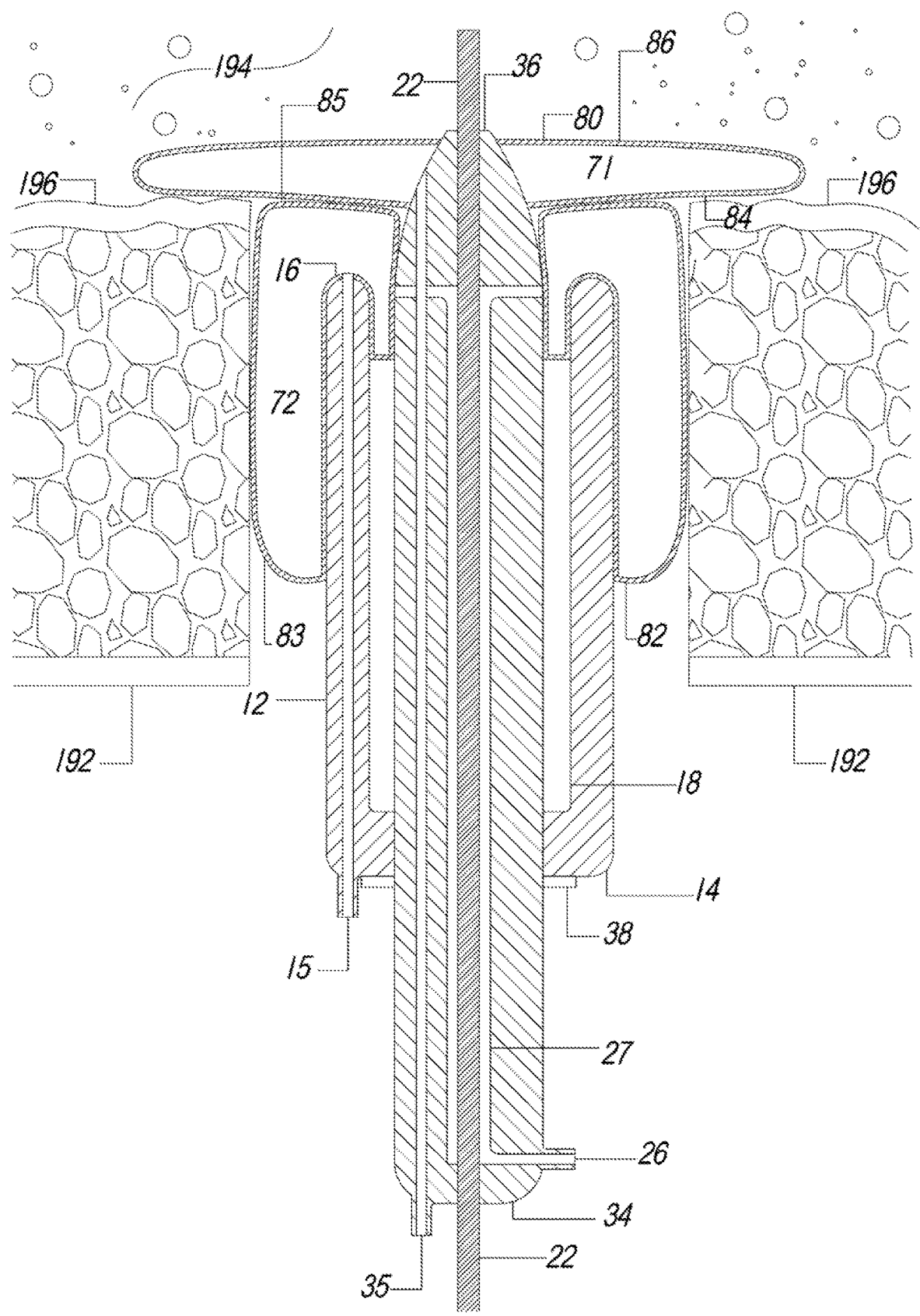
FIG. 6 is a schematic sectional representation of the embodiment of FIG. 3 in use showing an occlusion catheter advanced to the distal end of a puncture tract.
Figure 7:
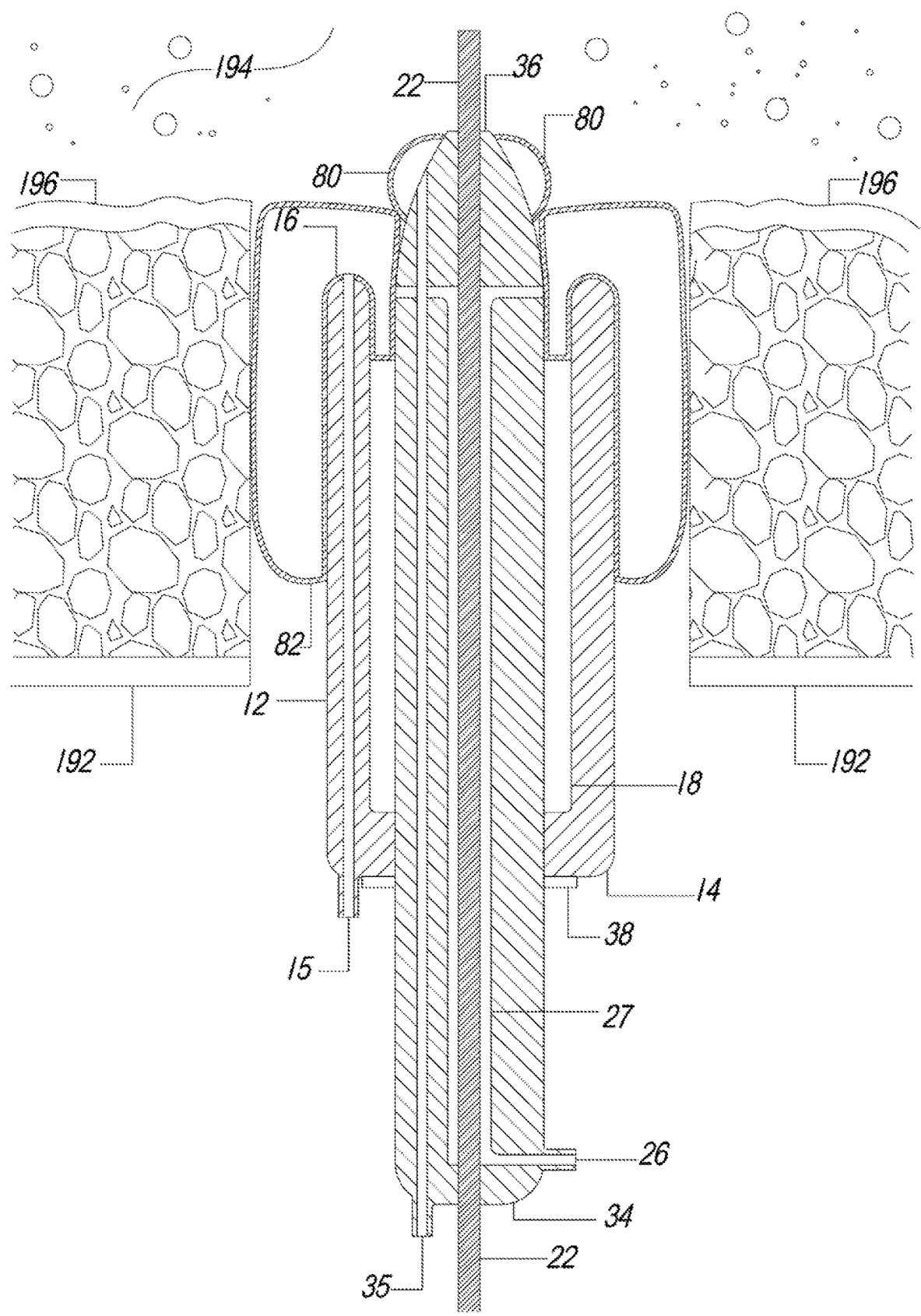
FIG. 7 is a schematic sectional representation of the embodiment of FIG. 3 in use showing an anchor balloon deflated and an inflated occlusion balloon.
Figure 8:
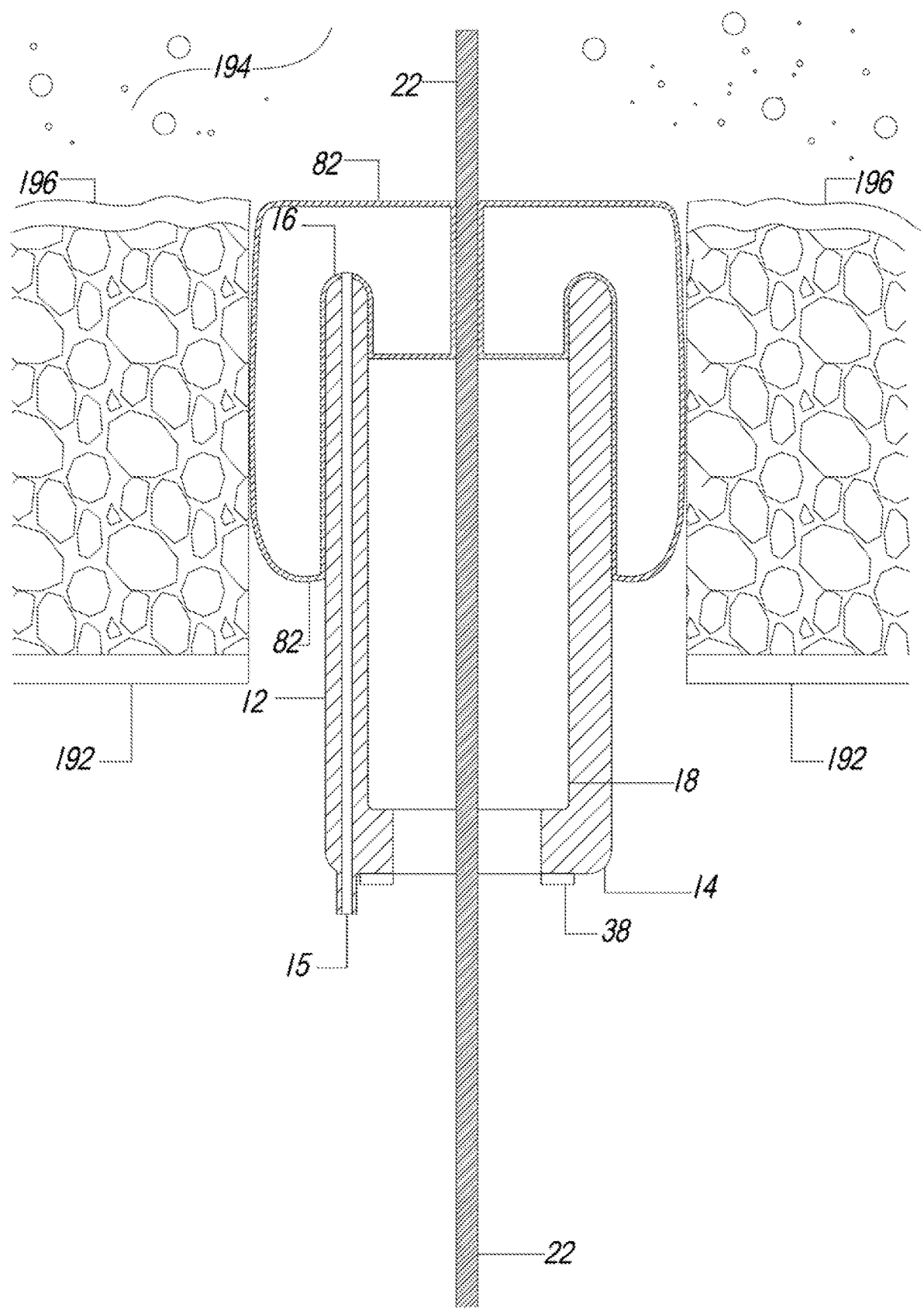
FIG. 8 is a schematic sectional representation of the embodiment of FIG. 3 in use showing an anchor catheter removed and an; occlusion balloon filling the vacated space.
Figure 9:
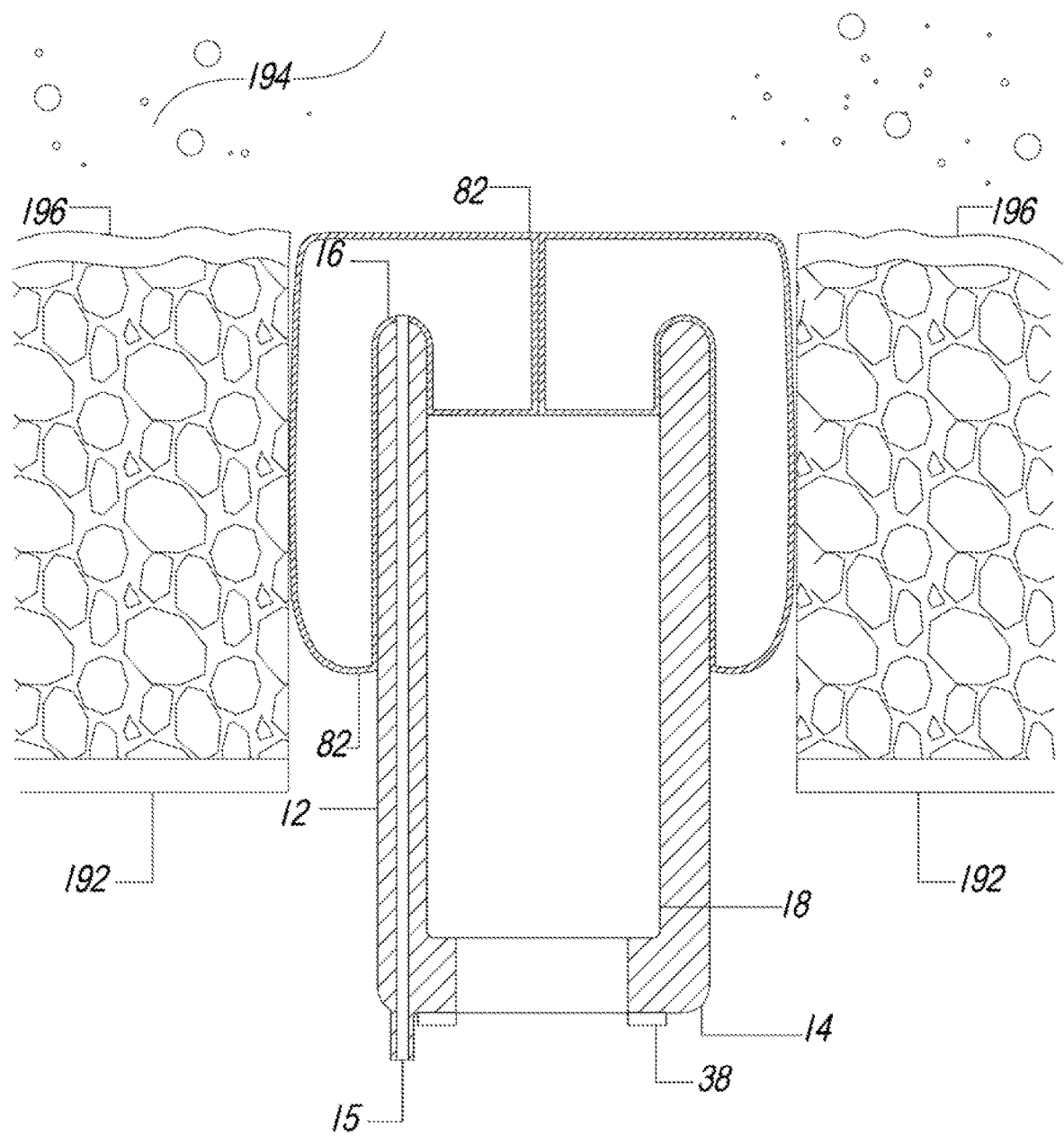
FIG. 9 is a schematic sectional representation of the embodiment of FIG. 3 in use showing a guidewire removed.
Figure 10:
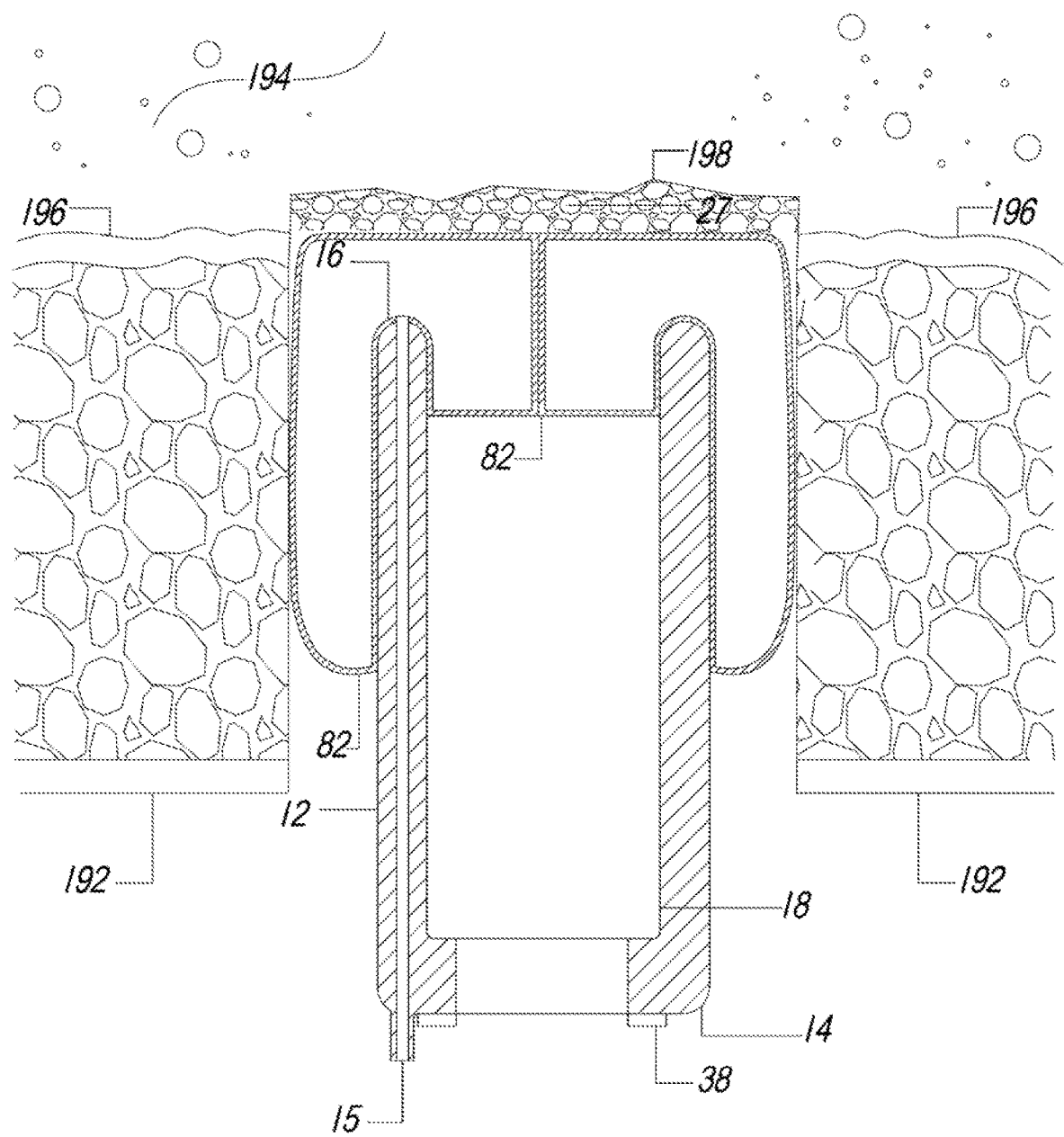
FIG. 10 is a schematic sectional representation of the embodiment of FIG. 3 in use showing a hemostatic layer has formed at a puncture site.
Figure 11:
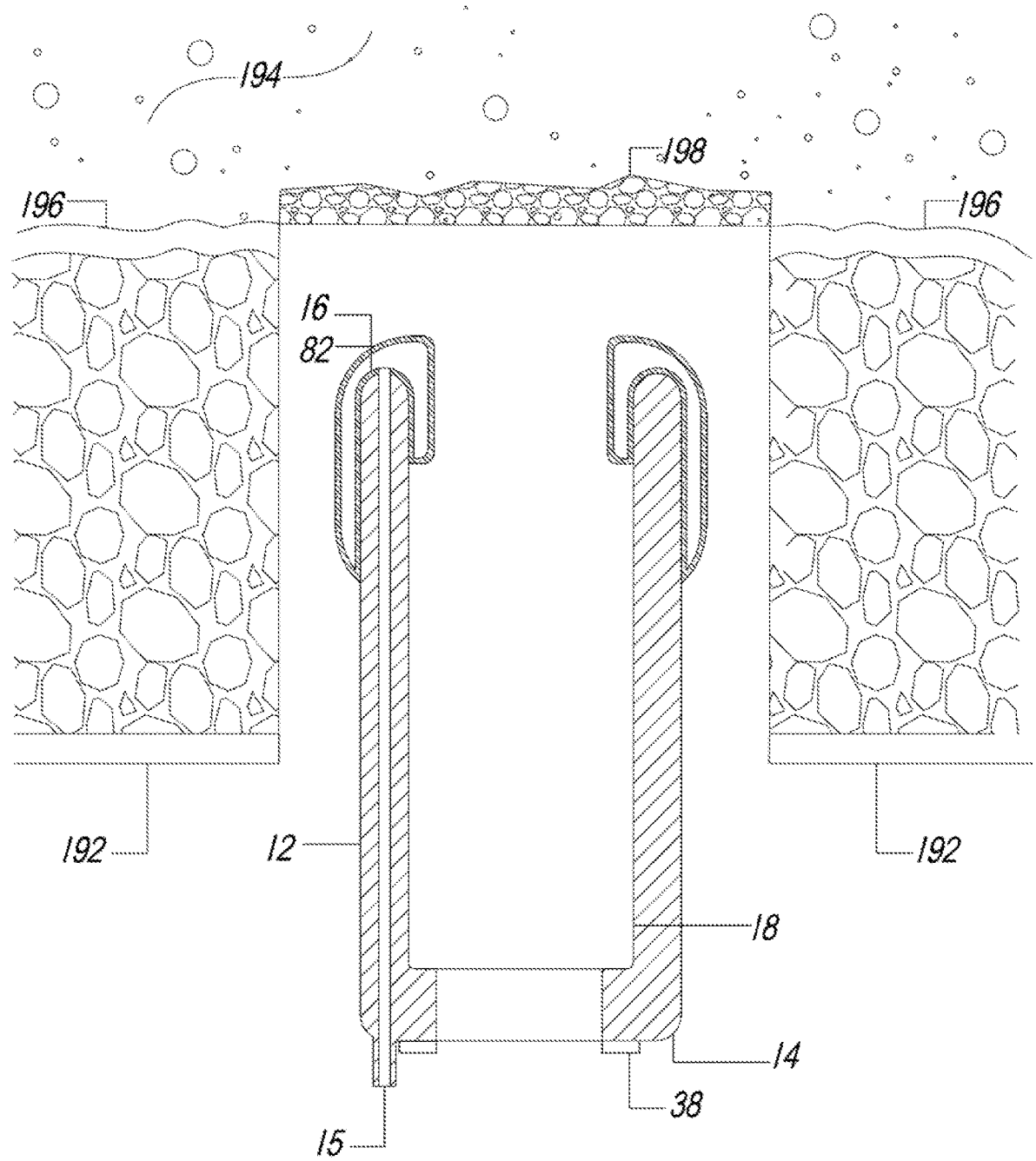
FIG. 11 is a schematic sectional representation of the embodiment of FIG. 3 in use showing an occlusion balloon deflated to assess the stability of a hemostatic layer that has formed at a puncture site.
Figure 12:
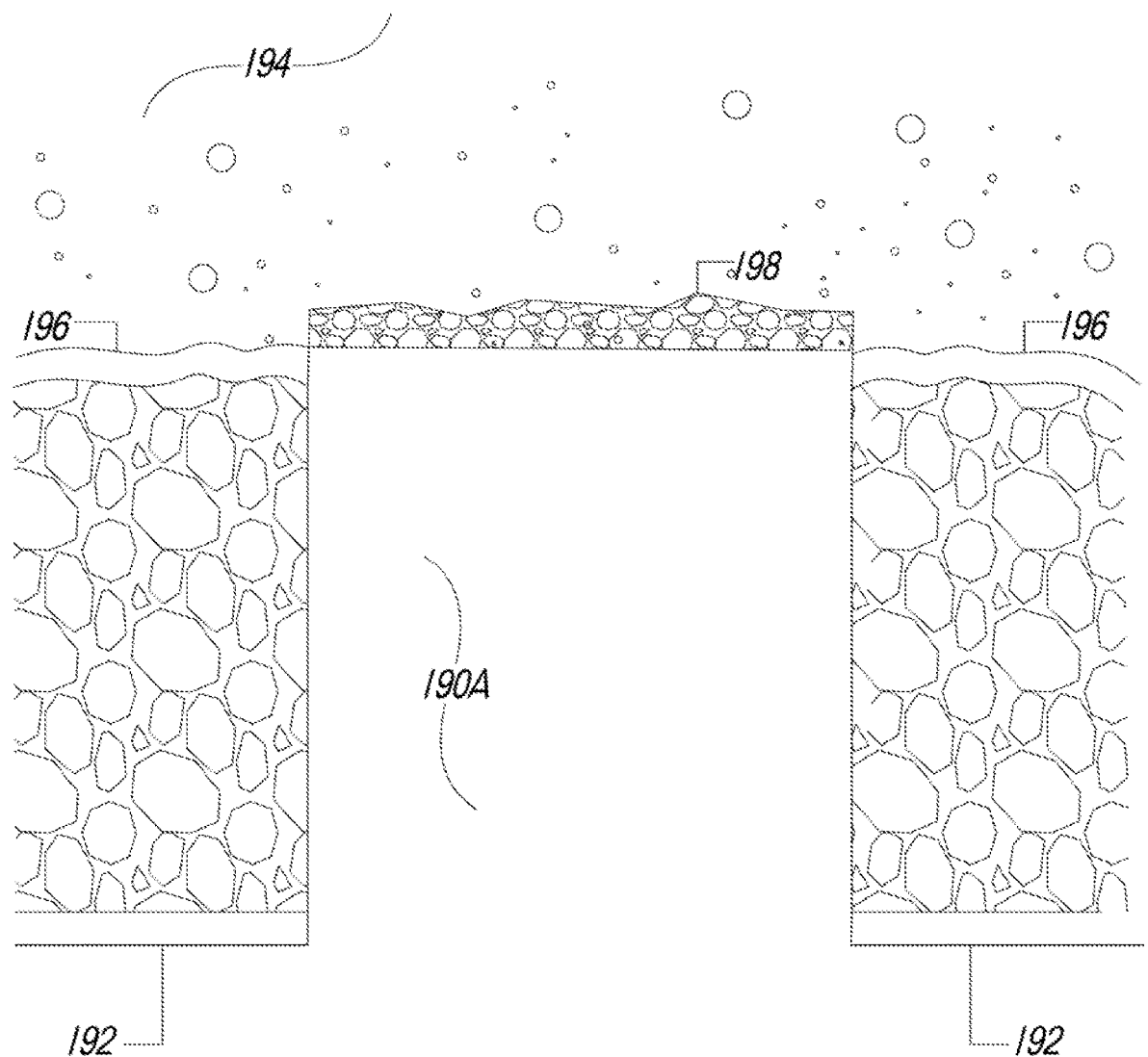
FIG. 12 is a schematic sectional representation of hemostasis confirmed after a balloon closure device has been removed, leaving behind a hemostatic plug.
Figure 13:
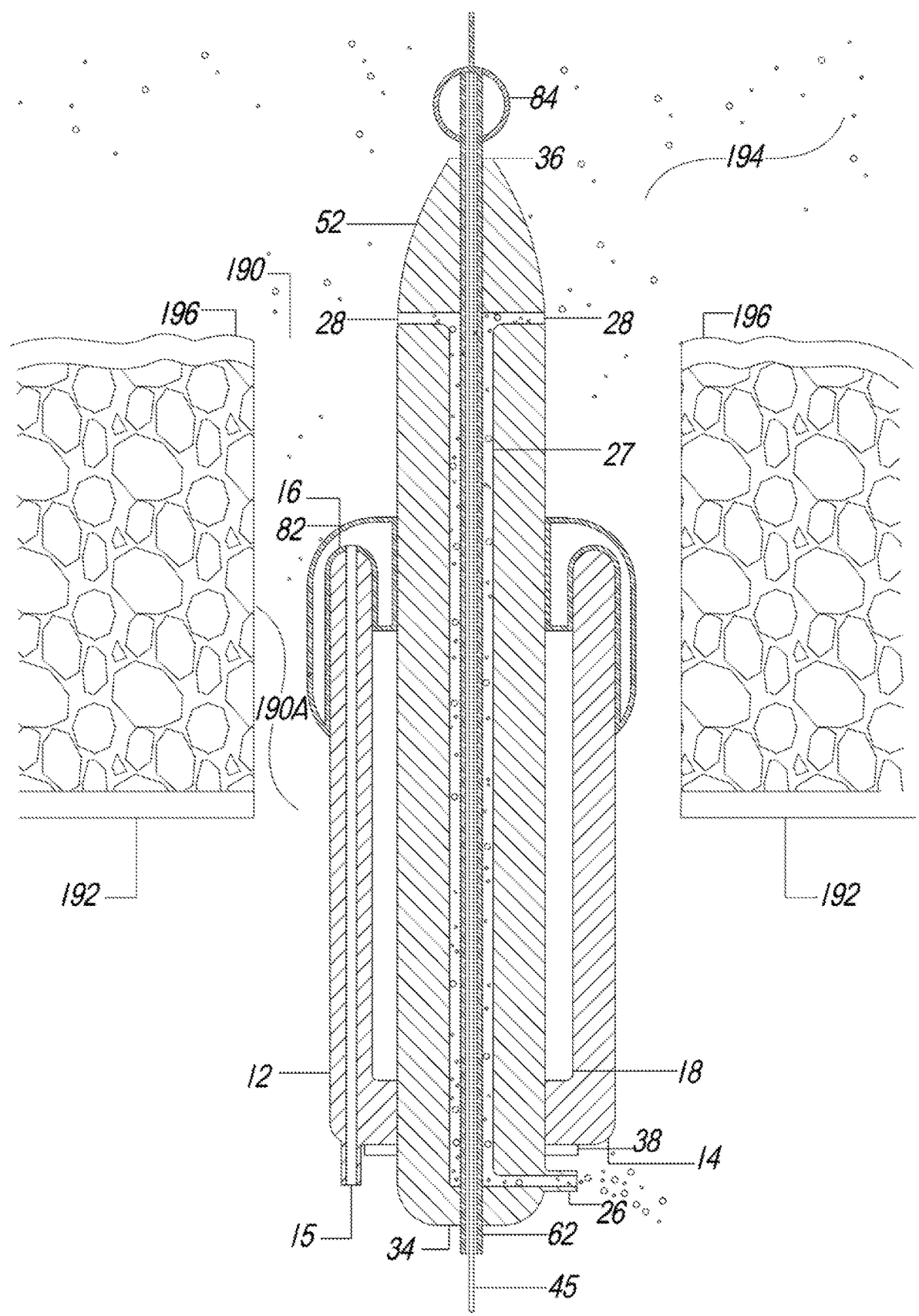
FIG. 13 is a schematic sectional representation of another embodiment of a system for sealing a puncture through tissue, in accordance with the present invention.

Briefly, FIG. 1 shows an embodiment of a system for sealing a puncture through tissue, in accordance with the present invention. FIG. 2 shows an operator inserting a guide wire 22 into a patient's blood vessel prior to the sealing of the puncture. FIG. 3 a balloon closure device 10, including the occlusion catheter 12 with its central anchor catheter/introducer 32. The anchor catheter/introducer 32 extends into the arterial lumen, and the occlusion catheter 12 resides in the puncture tract 190A. Both catheters 12, 32 have their balloons 82, 80 deflated. FIG. 4 shows the balloon closure device 10, shown as a cross-sectional illustration. In this embodiment, a vessel locator 28 demonstrates blood flow from the arterial lumen, confirming the anchor catheter's location in the arterial lumen 194. FIG. 5 shows an anchor balloon 82 inflated and the anchor catheter/introducer 32 pulled back, occluding the puncture 190. FIG. 6 shows the occlusion catheter 12 advanced to a distal end of the puncture tract 190A, abutting the inflated anchor balloon 80, and the occlusion balloon 82 is inflated to occlude the puncture 190 and the puncture tract 190A. FIG. 7 shows the anchor balloon 80 deflated and hemostasis, resulting from the inflated occlusion balloon 82, is assessed. FIG. 8 shows the anchor catheter 32 removed, the occlusion balloon 82 filling the vacated space, and hemostasis is assessed. FIG. 9 shows hemostasis being confirmed and the guidewire 22 is removed. In FIG. 10, a hemostatic layer has formed at the puncture site, adjacent to the inflated occlusion balloon. FIG. 11 shows the occlusion balloon 82 deflated to assess the stability of the hemostatic layer that has formed at the puncture site 190. In FIG. 12, hemostasis is confirmed and the balloon closure device 10 has been removed, leaving behind a hemostatic plug 198.

The balloon closure device 10 has particular utility when used in connection with intravascular procedures, such as angiographic dye injection, cardiac catheterization, balloon angioplasty and other types of recanalizing of atherosclerotic arteries, etc. since the balloon closure device 10 is designed to cause immediate hemostasis of the blood vessel, e.g., arterial, puncture. However, it is to be understood that while the description of the closure device is directed to the closing off of percutaneous incisions or punctures in arteries, it has much more wide-spread applications. Thus, the sealing of a percutaneous opening in an artery shown herein is merely exemplary.

Generally, the balloon closure device 10 includes an occlusion catheter 12, an anchor/introducer catheter 32 slidably coupled to the occlusion catheter 12, a hub connector 38 or other mechanism for biasing the anchor catheter 32 relative to the occlusion catheter 12, an anchor balloon or other expandable member 80, a vessel locator 28 coupled to the anchor catheter 32, and an occlusion balloon or other expandable member 82 coupled to the occlusion catheter 12. Ideally, the balloon closure device 10 will be able to use the anchor/introducer catheter 32 to facilitate passage of the balloon closure device through the puncture tract 190A and puncture 190, to reach the body lumen 194. Otherwise, a peel-away introducer sheath (not shown) may be needed to facilitate such passage.

With reference to FIGS. 1-12, the occlusion catheter 12 may be an elongate tubular body including a proximal end 14, a distal end 16, and a lumen 18 extending therebetween (shown in FIGS. 1-8), thereby defining a longitudinal axis. The occlusion catheter 12 may be flexible, semi-rigid, or rigid, e.g., having a uniform or variable flexibility along its length. The occlusion catheter 12 may be formed from a variety of materials providing a desired rigidity, e.g., plastic, such as polyamide, PEEK, nylon, PET, PEBAX, polyethylene, and/or metal, such as stainless steel or a nickel-titanium alloy, fabricated using known processes, e.g., extrusion, roll forming, machining, and the like. Optionally, a lubricious coating (not shown) may be provided on the exterior of the occlusion catheter 12, e.g., Dow 360 silicone fluid.

The distal end 16 of the occlusion catheter 12 may be is-attached to the occlusion balloon 82, as explained further below. The distal end 16 may be is-substantially flexible such that the distal end 16 may curve, bend, or otherwise conform substantially to the contour of the puncture tract 190A into which the distal end 16 is advanced. The occlusion catheter 12 is designed to preferentially remain in the puncture tract 190A and not extend into the puncture 190 and/or body lumen, and as such, it will not enlarge the diameter of the puncture hole. The distal end 16 of the occlusion catheter 12 may have a size sufficient to be inserted into a relatively small puncture tract. For example, the distal end 16 (and possibly the remainder of the occlusion catheter 12) may have an outer diameter between about 0.090-0.120 inch (2.28-3.05 mm). The minimum achievable dimensions of the balloon closure device and its components may be larger or smaller than mentioned herein. The balloon closure device and its components may be progressively scalable to correspond to the original sheath and puncture size.

The anchor catheter/introducer 32 may be used to facilitate passage of the balloon closure device 10. Alternatively, a peel-away introducer sheath (not shown) may be provided that is exchanged with the original sheath, to facilitate passage of the balloon closure device 10, and to facilitate subsequent sheath removal. Exemplary materials for the anchor catheter/introducer 32, and, if needed, the peel-away introducer sheath may include plastics, such as polyamide, PEEK, nylon, PET, PEBAX, and polyethylene, metals, such as stainless steel, and nickel titanium, and/or composite materials.

The anchor catheter/introducer 32, or the peel-away introducer sheath may enhance a rigidity and/or pushability of the balloon closure device 10, i.e., may be sufficiently rigid to support the balloon closure device 10, e.g., to prevent the balloon closure device 10 from buckling or kinking when being advanced through the puncture tract, across a puncture, and into the body lumen, as desired. The anchor catheter/introducer 32 is designed to advance across the puncture 190, and into the body lumen.

In addition, the peel-away introducer sheath may be used to exchange one balloon closure device 10 for another, e.g., in the event that the anchor balloon 80 ruptures or if a different size anchor balloon is desired. Furthermore, the peel-away introducer sheath may include a side port (not shown) on its proximal end for delivering a fluid.

With continued reference to FIGS. 1-12, the anchor catheter/introducer 32 may be an elongate body including a proximal end 34, and a distal end 36. As can be seen in FIGS. 3-7, the anchor catheter 32 is slidably received within the lumen 18 of the occlusion catheter 12 such that the distal end 36 of the anchor catheter 32 extends beyond the distal end 16 of the occlusion catheter 12. The lumen 18 of the occlusion catheter 12, may have an inner diameter between about 0.068-0.076 inch (1.73-1.93 mm).

When the anchor catheter 32 is disposed within the lumen 18, the distal end 36 of the anchor catheter 32 may extend substantially beyond the distal end 16 of the occlusion catheter 12. The distal end 36 of the anchor catheter 32 may be attached to the anchor balloon 80, as explained further below. The distal end 36 of the anchor catheter 32 may be tapered and may terminate in a substantially flexible and/or atraumatic distal tip, e.g., a "J" tip and the like (not shown).

The anchor catheter 32 may be a hollow wire, hypotube, catheter, and/or the like, formed from a variety of materials, e.g., plastic and/or metal, similar to the occlusion catheter 12. For example, the distal end 36 (and possibly the remainder of the anchor catheter 32) may be polymeric having an outer diameter between about 0.065-0.073 inch (1.65-1.85 mm), and therefore able to pass through the lumen 18 of the occlusion catheter 12. The anchor catheter 32 may include a lumen for receiving a guidewire 22 therethrough, e.g., such that the anchor catheter 32 may be advanced over a guidewire. The guidewire may have an outer diameter between about 0.021-0.025 inch (0.53-0.64 mm). Larger scaled versions of the balloon closure device 10 may accommodate a standard guidewire with an outer diameter of about 0.035 inch (0.89 mm).

The anchor catheter 32 may be biased to move distally relative to the occlusion catheter 12, so that the anchor catheter 32 may pass through the puncture and enter the body lumen, while the occlusion catheter 12 may remain within the puncture tract.

Turning to FIG. 3, the hub connector 38 may be provided for biasing the anchor catheter 32 relative to the occlusion catheter 12. The hub connector 38 may include cooperating connectors, e.g., hemostatic y connectors (not shown), that may be used for flushing a fluid through the occlusion catheter lumen 18, and for reversibly locking the occlusion catheter 12 to the inner nested anchor catheter 32, as needed. Generally, the hub connector 38 may extend from the proximal end 14 of the occlusion catheter 12. For example, the hub connector 38 may be attached to the proximal end 14 of the occlusion catheter 12 using an adhesive, an interference fit, mating threads, and the like, e.g., to substantially permanently attach the hub connector 38 to the proximal end 14 of the occlusion catheter 12. With the hub connector 38 attached to the occlusion catheter 12, the side port (not shown) may communicate with the occlusion catheter lumen 18. Thus, fluid delivered into the side port may enter the lumen 18.

The side port (not shown) may include a connector, e.g., a luer lock connector, or a nipple (not shown) for connecting tubing or otherwise connecting a source of fluid (not shown) to the side port. For example, a syringe (not shown) filled with fluid, e.g., saline, and the like, may be connected to the side port for manually delivering the fluid into the lumen 18. Alternatively, a pump or other device (not shown) may be provided for delivering fluid at a desired pressure and/or flow rate.

The hub connector 38 may include a hemostatic connector (not shown) with an adjustable central aperture (not shown). The distal end 36 of the anchor catheter 32 may be inserted into the aperture, allowing the anchor catheter 32 to pass through the occlusion catheter lumen 18, across the puncture, and into the body lumen. The anchor catheter 32 may be fixed in an axial position relative to the occlusion catheter 12, by tightening the central aperture of the hemostatic connector of the hub connector 38, for example, using a compression spring, a hemostatic valve, or other mechanism, as is known in the art. The proximal ends of the occlusion catheter 12 and anchor catheter 32, may each include annular bands or other markers (not shown) thereon that may become aligned when the distal ends of the catheters are offset as desired, as discussed below.

The anchor balloon 80 and the occlusion balloon 82 may each be inflated by using a viscous fluid (i.e., a fluid more viscous than air). This should avoid the introduction of any significant amount of air into any body lumen where air does not belong. Preferentially, fluid may be injected into the balloon using a predetermined volume that will achieve a desired balloon diameter based on the balloon's compliance characteristics. If a predetermined pressure is needed for proper balloon inflation, then some type of visual indication or gauge may be provided to indicate that the predetermined pressure has been reached. The predetermined pressure may correspond to a desired maximum pressure for a balloon, e.g., to ensure that the balloon is expanded to a desired diameter and/or to prevent risk of the balloon rupturing.

Turning to FIGS. 3-11, the anchor balloon 80 and the occlusion balloon 82 may each be reversibly expandable from a collapsed state to an expanded state when an inflation medium (not shown) is introduced into the interior of each balloon. In an alternative embodiment, other expandable members, e.g., a mechanically expandable or self-expanding member (not shown) may be provided instead of a balloon.

The balloons 80 and 82 may each be formed from a flexible, substantially inelastic material, e.g., a nonelastomeric material, such as PET, nylon, PEBAX, and the like, that may provide a substantially noncompliant balloon that may expand to a predetermined size once a minimum pressure is introduced into the interior. In this embodiment, the size of the balloons 80 and 82 in the expanded state may be fixed. Alternatively, the balloons 80 and 82 may each be formed from an elastic material, such as POC, polyethylene, polyurethane, silicone, and the like, such that the size of the balloons 80 and 82 in the expanded state is dependent upon the volume of fluid delivered within the interior, as is known in the art.

In one embodiment, as seen in FIG. 6, the anchor balloon 80 includes a proximal end 84, a distal end 86, and an expandable intermediate section defining the interior 71 of the anchor balloon 80. The proximal and distal ends 84 and 86, respectively, of the anchor balloon 80 may be attached to the distal end 36 of the anchor catheter 32, but, preferably, proximal to its tapered tip. The interior 71 of the anchor balloon 80 may communicate with the balloon inflation lumen 35 of the anchor catheter 32. Similarly, the occlusion balloon 82 includes a proximal end 83, a distal end 85, and an expandable intermediate section defining the interior 72 of the occlusion balloon 82. The proximal end 83 of the occlusion balloon 82 may be attached to the distal end 16 of the occlusion catheter 12, and the distal end 85 of the occlusion balloon 82 may be attached to or may extend beyond the distal end 16 of the occlusion catheter 12. The interior 72 of the occlusion balloon 82 may communicate with the balloon inflation lumen 15 of the occlusion catheter 12.

As can be seen, in FIG. 6, the proximal and distal ends 84 and 86, respectively, of the anchor balloon 80 may overlie and be attached to the distal end 36 of the anchor catheter 32, e.g., using an adhesive, sonic welding, crimping, a compressive sleeve, an interference fit, and/or the like. Similarly, the proximal and distal ends 83 and 85, respectively, of the occlusion balloon 82 may overlie and be attached to the distal end 16 of the occlusion catheter 12, e.g., using an adhesive, sonic welding, crimping, a compressive sleeve, an interference fit, and/or the like.

The distal end 86 of the anchor balloon 80 may be attached proximal to the tapered portion of the anchor catheter 32 and not extend beyond the distal end 36 of the anchor catheter 32, e.g., to allow for the least diameter profile for the distal tip of the anchor catheter 32. The anchor balloon 80 may have a length of at least about five millimeters (5 mm). The distal end 85 of the occlusion balloon 82 may extend beyond and wrap around the distal end 16 of the occlusion catheter 12, and extend into the occlusion catheter lumen 18. This design may allow the occlusion balloon to inflate and atraumatically occlude both the puncture and the puncture tract, over time facilitating hemostasis within a puncture in a wall of a body lumen. The occlusion balloon 82 may have a length of at least about twenty millimeters (20 mm) on the outer surface of the occlusion catheter 12 and possibly a length of at least about ten millimeters (10 mm) on the inner luminal surface of the occlusion catheter 12. This length is based on the punctured blood vessel and the length of its associated puncture tract requiring occlusion, e.g. the femoral artery versus the radial artery which has a very short puncture tract.

In the collapsed state, shown in FIGS. 3 and 4, the anchor and occlusion balloons 80 and 82, respectively, may conform substantially to the diameter of the anchor and occlusion catheters 32 and 12, respectively. The anchor balloon 80 is expanded to the expanded state, shown in FIGS. 5 and 6, by introducing an inflation medium (not shown) into the balloon inflation lumen 35 of the anchor balloon 80, and consequently into the interior 71 of the anchor balloon 80. The occlusion balloon 82 is expanded to the expanded state, shown in FIGS. 6-10, by introducing an inflation medium (not shown) into the balloon inflation lumen 15 of the occlusion balloon 82, and consequently into the interior 72 of the occlusion balloon 82. The balloon inflation lumens may each include one or more seals (not shown), separate lengths of tubing, a hemostatic adapter, stopcock, and the like, attached, to its proximal end, e.g., to prevent substantial proximal flow of fluid through the lumen and to maintain balloon inflation pressure, as is known in the art.

Optionally, not shown, the balloon closure device 10 may include other components, e.g., to provide a kit for performing a procedure on a patient. For example, an introducer sheath, such as a valved hemostatic peel-away introducer sheath, may be provided that includes a proximal end, a distal end, and a lumen extending therebetween. The introducer sheath may include a dilator with a tapered distal tip that may be inserted into the lumen of the introducer sheath, e.g., for facilitating advancing the introducer sheath through a puncture, as is known to those skilled in the art. In addition, the introducer sheath may include a side port on the proximal end communicating with the lumen and/or may include one or more seals (not shown), e.g., to prevent substantial proximal flow of fluid through the lumen, as is known in the art. The side port may include one or more components, e.g., separate lengths of tubing, stopcocks and the like (not shown), as will be appreciated by those skilled in the art. In addition, the kit may include a syringe, not shown, or other device for delivering fluid into the side port of the introducer sheath, as well as for delivering inflation medium into the balloon inflation lumens, as explained above. A syringe may be connected to the side port of the introducer sheath for injecting fluid into the introducer sheath lumen, and similarly into ports located on the proximal ends of the balloon inflation lumens.

Optionally, the kit may also include a stylet or obturator (not shown) that may be inserted into the lumen of the introducer sheath, e.g., to facilitate percutaneously inserting the introducer sheath through tissue, as is known to those skilled in the art. In addition, or alternatively, one or more guidewires (not shown) may also be provided.

Turning to FIGS. 1-21, a method for sealing a passage through tissue is shown. The passage may be a percutaneous puncture extending from a patient's skin to a blood vessel or other body lumen. For example, the vessel may be a peripheral artery or vein, e.g., a femoral artery, a femoral vein, a carotid artery, and the like.

Before further describing the use of the balloon closure device 10 to seal a puncture, a brief description of a typical, conventional, intravascular surgical procedure, e.g., catheter instrumentation of an artery, utilizing a percutaneous opening will be given to best appreciate the features of the invention. In such a procedure a cannula of an instrument, such as an angiographic needle (not shown), is inserted percutaneously through the skin into the artery, such as the femoral artery, at the situs for the closure device's insertion. The needle cannula is held in place and the flexible end of a mini-guidewire (not shown) is then passed through the cannula into the artery to the desired depth (i.e., longitudinal position therealong). Once the mini-guidewire is in place the needle cannula is removed, leaving the guidewire in place.

An introducer sheath (not shown) and an arterial dilator (not shown) are then passed over the guidewire, through the puncture or incision and into the artery. The guidewire and then the dilator are removed leaving the introducer sheath in place.

One or more instruments (not shown) may be advanced through the introducer sheath and into the vessel, e.g., to perform a diagnostic and/or therapeutic procedure within the patient's body, e.g., threaded down the artery to the desired intravascular location, e.g., the situs of the atherosclerotic occlusion. The one or more instruments may include catheters, e.g., balloon catheters, stent delivery catheters, imaging catheters, and the like, guidewires, and/or other devices. Upon completing the intravascular procedure(s), any instruments may be removed. Thereafter, the sheath is removed and a physician or other trained person applies manual, digital pressure to the percutaneous puncture until hemostasis has occurred. In particular, the current standard of care for puncture hemostasis is to apply digital or mechanical pressure on the puncture site for twenty minutes to an hour, depending on the puncture size and the degree of hemolytic therapy. Obviously, this results in wasted time for the physicians and other catheter lab personnel, and causes inconvenience and discomfort for the patient. In addition, serious complications arise from persistent bleeding and hematoma formation in approximately five percent of the patients. A much better option is to employ a system to seal the arterial puncture site 190 and plug the puncture tract 190A, such as that shown in FIGS. 1-21 and described above. Moreover, as will be appreciated from the description to follow, the balloon closure device 10 is designed to reduce post-procedure puncture complications, cause minimal inflammatory reaction, and leave nothing behind in the vessel or puncture tract.

Turning to FIGS. 3 and 4, with the anchor and occlusion balloons, 80 and 82, respectively, in the collapsed state, and using the anchor catheter 32 as an introducer, the balloon closure device 10 may be inserted through the puncture tract lumen 190A, over the device exchange guidewire 22, until the anchor catheter's distal end has passed through the puncture 190 and is disposed within the vessel 194. This may be indicated by blood entering intraluminal ports referred to as vessel locator distal holes 28, passing through a marker lumen 27, and exiting the vessel locator proximal hole 26. The distal holes, marker lumen, and proximal hole are all part of the anchor catheter 32. The marker lumen allows a pathway for back-bleeding (obtaining mark) from the body lumen, e.g., a femoral artery, to ensure proper device positioning.

Optionally, the balloon closure device 10 may include one or more markers, e.g., radiopaque markers (not shown), to facilitate monitoring insertion of the system 10 using external imaging, e.g., fluoroscopy, ultrasound, magnetic resonance imaging ("MRI"), and the like.

Alternatively or in addition, one or more visual markers (not shown) may be provided, e.g., on the proximal end 34 of the anchor catheter 32, and on the proximal end 14 of the occlusion catheter 12, respectively. The markers may include one or more colored bands at predetermined locations along a length of the anchor catheter 32 relative to the anchor balloon 80. For example, a distance between a band on the proximal end 34 of the anchor catheter 32 may correspond to a length of the anchor catheter 32, thereby providing a visual indication when the anchor catheter 32 has been advanced sufficiently to expose the anchor balloon 80 beyond the distal end 16 of the occlusion catheter. Similarly, the markers may include one or more colored bands at predetermined locations along a length of the occlusion catheter 12 relative to the distal end 16 of the occlusion catheter 12, with the distance between bands corresponding to the length of insertion of the occlusion catheter 12 into the puncture tract 190A. Together, these markers may provide a visual indication when the balloon closure device 10 has been advanced sufficiently through the puncture and into the vessel lumen.

As shown in FIGS. 4 and 5, once the anchor balloon 80 is disposed within the vessel lumen and blood is exiting the vessel locator proximal hole 26, the anchor balloon 80 may be expanded to the expanded state, e.g., by introducing fluid into the balloon inflation lumen 35 through the anchor catheter 32 and into the anchor balloon 80. A prescribed amount of fluid may be introduced so that the anchor balloon 80 may be expanded to a desired size. An additional mechanism may be provided to inform the user that a desired pressure has been reached within the anchor balloon. In addition, one or more mechanisms may be provided to prevent deflation of the anchor balloon including a stopcock, and possibly a hemostatic valve connected to the balloon inflation lumen. The hemostatic valve may have a quick connect adapter requiring a syringe to be attached and locked into the adapter before inflation or deflation may occur.

The anchor catheter 32 may be removed, if desired. For example, if the anchor balloon 80 accidentally ruptures, the anchor catheter 32 may be removed and replaced with another anchor catheter having an intact balloon (not shown). In addition or alternatively, if it is discovered that the anchor balloon 80 is the wrong size for the given anatomy (e.g., is too small for the puncture or too large for the vessel), the anchor catheter 32 may be replaced with one having a larger or smaller balloon. This may be avoided by the anchor balloon 80 having a range of possible sizes based on its degree of inflation.

As shown in FIG. 5, the anchor catheter 32 may be partially withdrawn from the arterial lumen with the anchor balloon 80 in the expanded state, i.e., until the anchor balloon 80 engages (catches) on the artery wall contiguous with the puncture. Preferably, the anchor balloon 80 substantially seals the puncture 190, i.e., substantially isolating the puncture 190 from the arterial lumen 194. Thus, the balloon closure device 10 may provide temporary hemostasis, e.g., preventing blood from passing through the puncture 190. Thus, even without the additional steps that follow, the balloon closure device 10 may be used to provide hemostasis in emergency situations in order to minimize loss of blood until a puncture victim may be treated.

The anchor balloon 80 in the expanded state, as described above, may be particularly suited for providing hemostasis, while still allowing blood flow to continue along the arterial lumen 194. For example, as shown in FIG. 5, the diameter of the anchor balloon 80 may be substantially greater than its length in the expanded state. Thus, when the anchor balloon 80 is pulled into engagement with the arterial wall 196 of the arterial lumen 194, at least a portion of the arterial lumen 194 may remain unobstructed, as shown.

As shown in FIG. 6, with an individual applying a proximal force to the anchor catheter 32 in order to maintain the anchor balloon 80 substantially against the puncture 190, the occlusion catheter 12 may be advanced to the distal end of the puncture tract 190A and the anchor catheter 32 and occlusion catheter 12 may be locked together at the hub connector 38. While reapplying a proximal force to the anchor catheter 32 in order to maintain the anchor balloon 80 substantially against the puncture 190, the occlusion balloon 82 may be inflated against the exterior of the artery contiguous with the puncture 190 to occlude the puncture and the puncture tract 190A. The balloon closure device 10 is now essentially locked in place in the puncture tract. If needed, a tensioner (not shown) may be provided that may apply a proximal force to the anchor catheter 32 to maintain the anchor balloon 80 substantially against the puncture 190. The tension imposed by the tensioner may apply a desired tensile force to the anchor balloon 80 to maintain hemostasis while preventing the anchor balloon 80 from being pulled into the puncture 190 and/or preventing the arterial wall 196 of the arterial lumen 194 from excessive tenting.

The occlusion balloon 82 may optionally be coated with a hemostasis-promoting material (not shown), e.g. chitosan, which may promote hemostasis within the puncture tract 190A. Because of the hemostasis provided by the anchor balloon 80, the hemostasis-promoting material on the occlusion balloon may be delivered to the puncture tract without substantial concern that the hemostasis-promoting material may leak into the arterial lumen 194.

As shown in FIGS. 7 AND 8, once the occlusion balloon 82 is fully inflated, the anchor balloon 80 may then be deflated to the collapsed state, and hemostasis may be assessed. Once hemostasis is confirmed, the anchor catheter 32 may then be withdrawn from the puncture 190, into the puncture tract 190A, and removed from the body. Similarly, as shown in FIG. 9, the device exchange guidewire 22 may be withdrawn from the puncture 190, into the puncture tract 190A, and removed from the body.

A syringe or other device (not shown) may be used to evacuate fluid via the side port of the balloon inflation lumen 35 to collapse the anchor balloon 80. Once fluid is removed, and the anchor balloon 80 is in the collapsed state, the anchor balloon 80 may be withdrawn through the puncture 190 and puncture tract 190A without substantially disturbing the inflated occlusion balloon 82. To facilitate removing the anchor balloon 80, a lubricious coating (not shown) may be provided on the exterior of the anchor balloon 80, e.g., Dow 360 silicone fluid. Such a coating may prevent the anchor balloon 80 from sticking to or otherwise pulling on the occlusion balloon 82 as the anchor balloon 80 is withdrawn.

The occlusion balloon may remain inflated in the tissue tract for a time duration based on patient-related factors including the size of the puncture and the patient's level of anticoagulation. This time duration may range from minutes to hours. With very large punctures, maintaining puncture tract occlusion overnight may also be a suitable option, while still allowing unobstructed blood flow to continue along the arterial lumen 194. It may be possible that, with the occlusion balloon inflated, a patient may ambulate without compromising the hemostatic process.

As shown in FIGS. 10 and 11, after sufficient time has elapsed, the occlusion balloon 82 may be deflated and hemostasis assessed, possibly both at rest and with ambulation. As shown in FIG. 12, once hemostasis is confirmed, the balloon closure device 10 may be completely removed from the body, leaving nothing behind but the body's own hemostatic plug 198.

Figure 14:
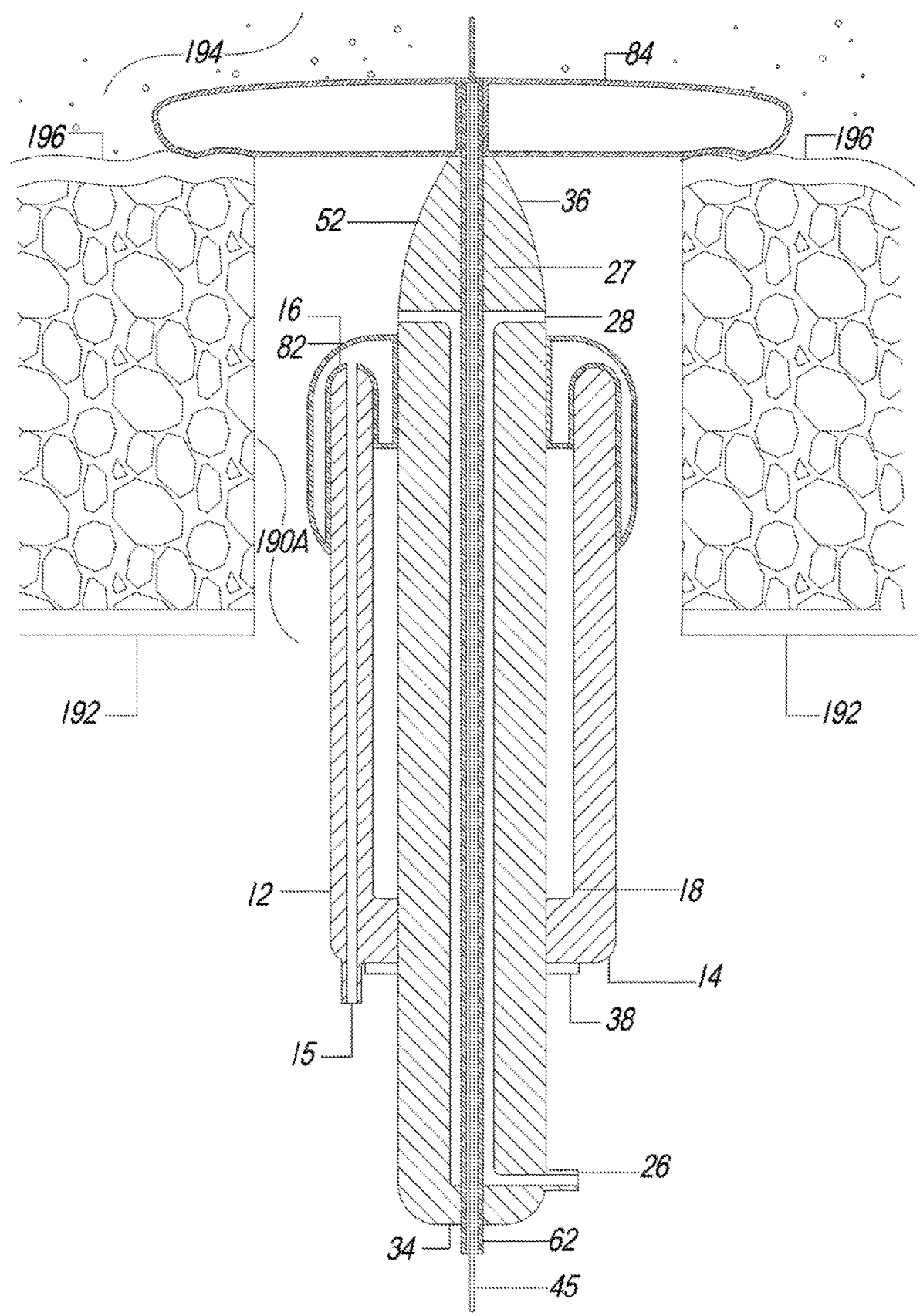
FIG. 14 is a schematic sectional representation of the embodiment of FIG. 13 in use showing an alternative anchor balloon.
Figure 15:
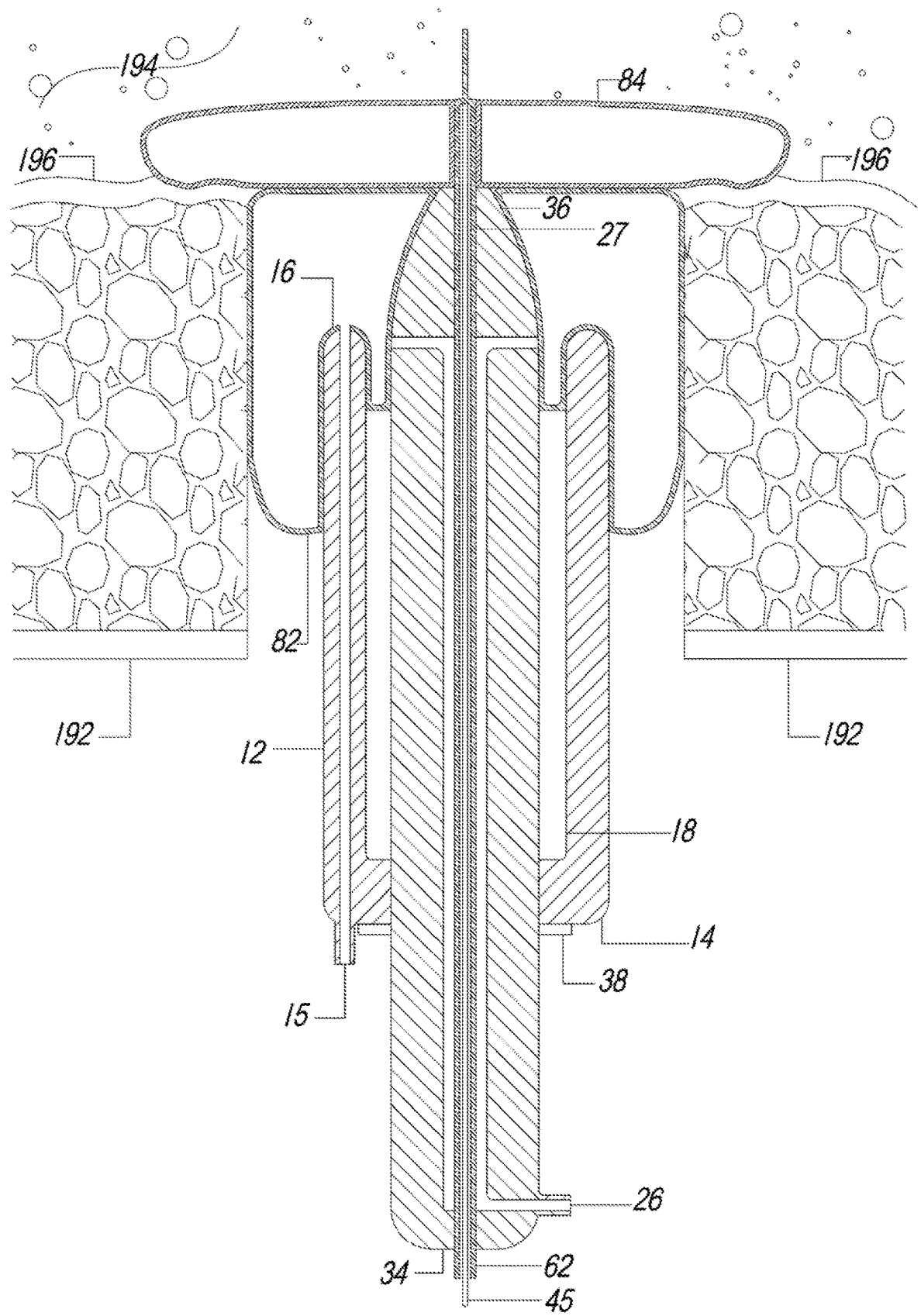
FIG. 15 is a schematic sectional representation of the embodiment of FIG. 13 in use showing an occlusion catheter is-advanced to the distal end of a puncture tract.
Figure 16:
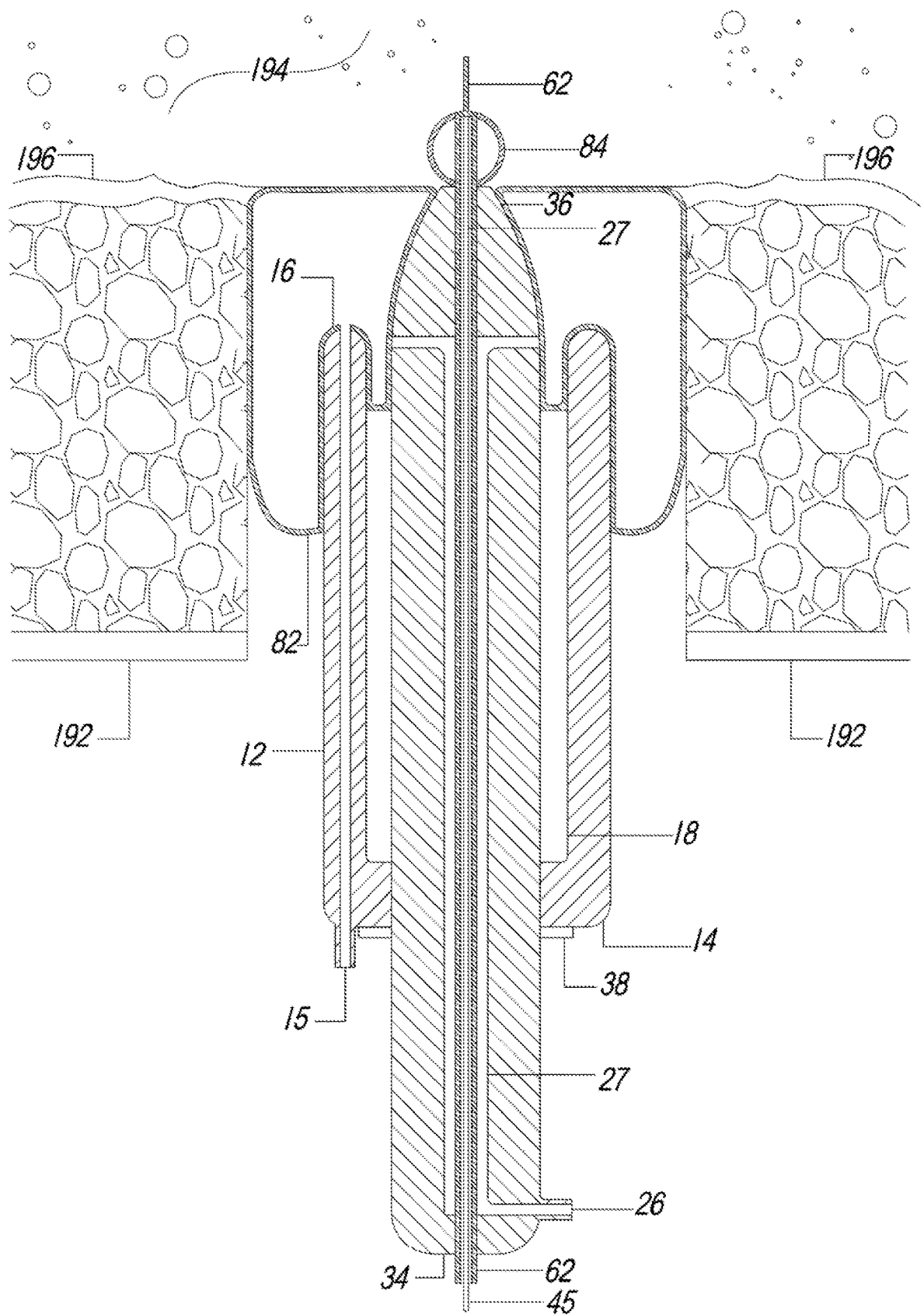
FIG. 16 is a schematic sectional representation of the embodiment of FIG. 13 in use showing an alternative anchor balloon deflated and an inflated occlusion balloon.
Figure 17:
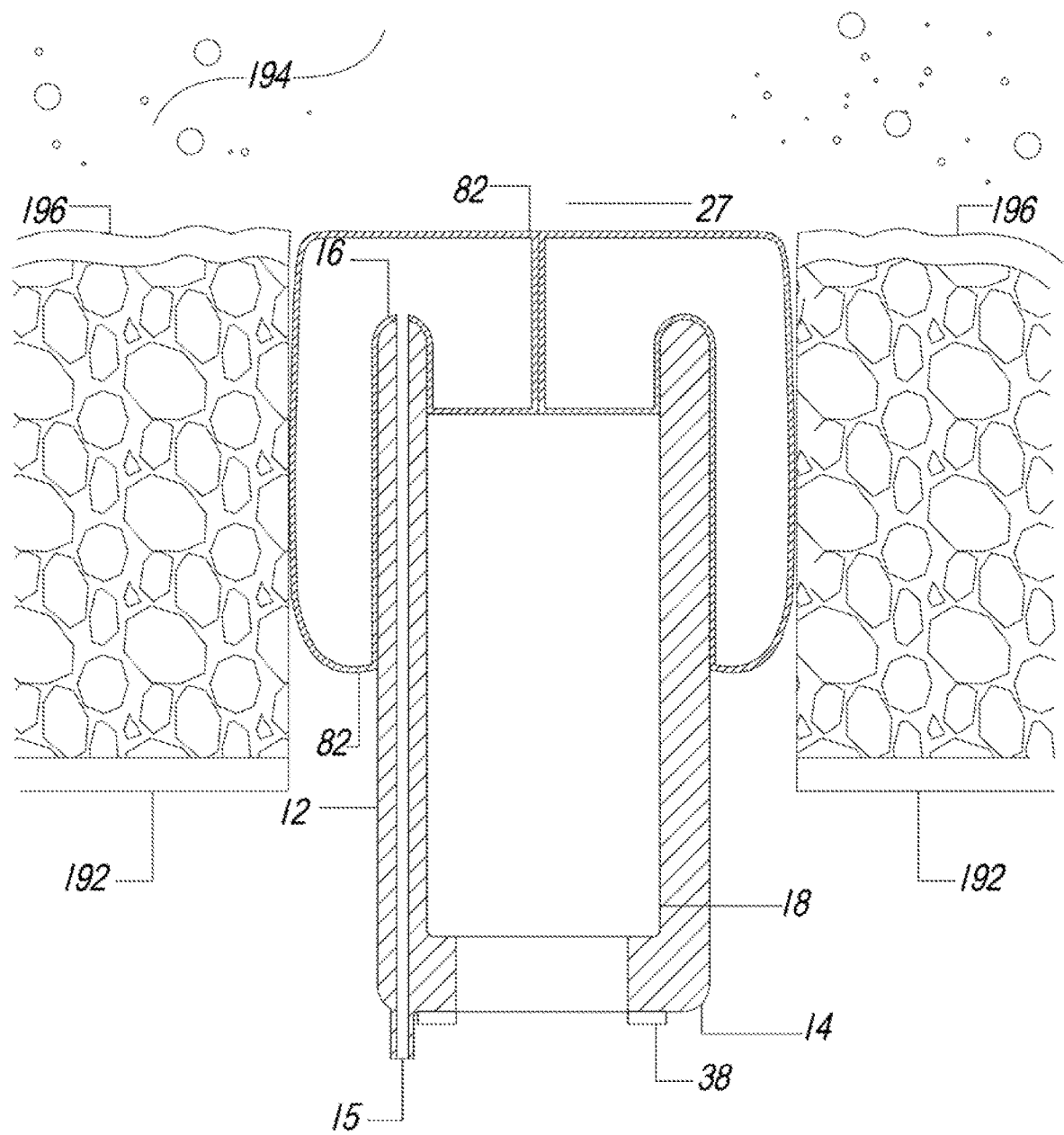
FIG. 17 is a schematic sectional representation of the embodiment of FIG. 13 in use showing a dilator/introducer and alternative anchor balloon are removed and an occlusion balloon filling the vacated space.
Figure 18:
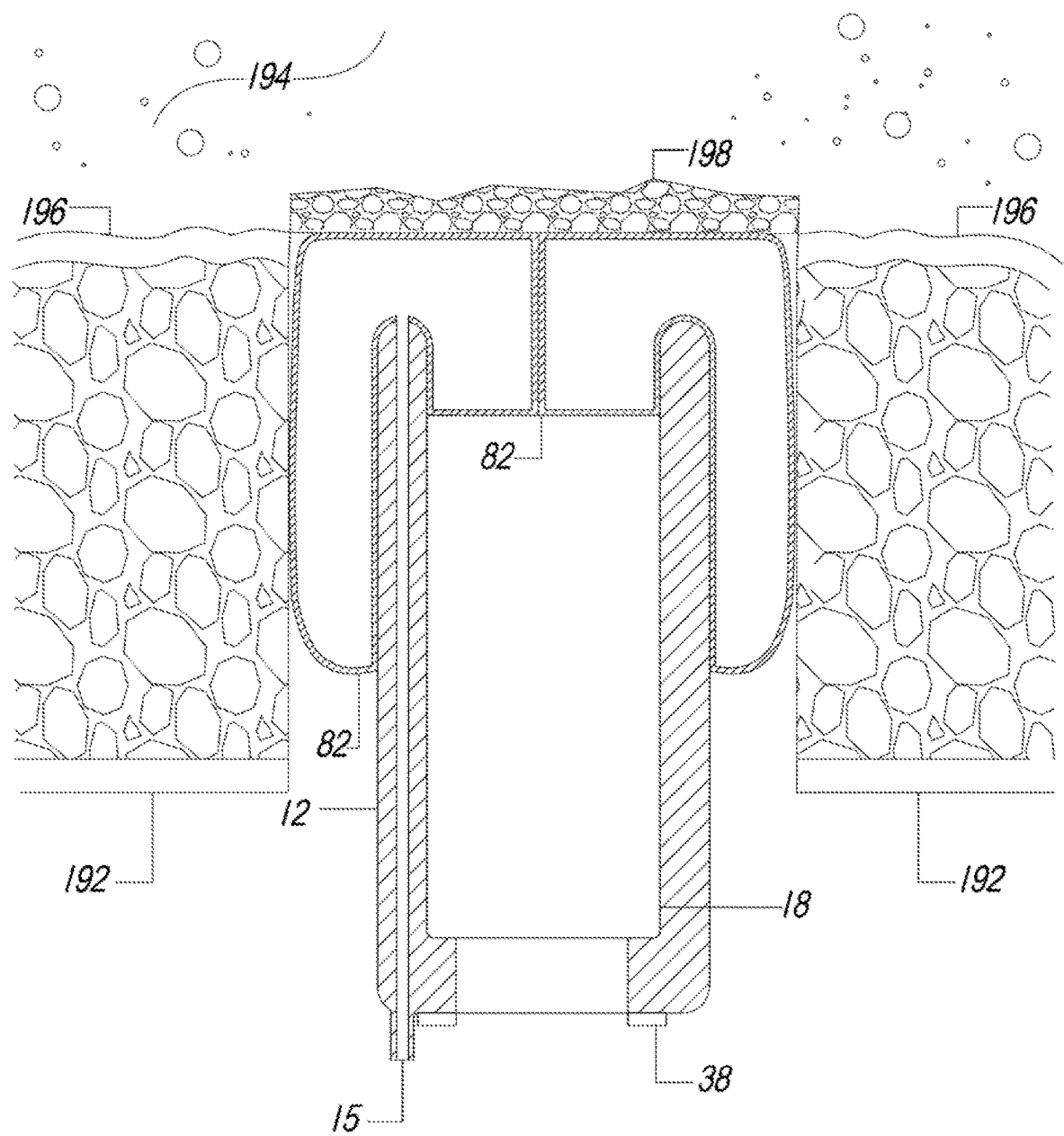
FIG. 18 is a schematic sectional representation of the embodiment of FIG. 13 in use showing a hemostatic layer formed at a puncture site.
Figure 19:
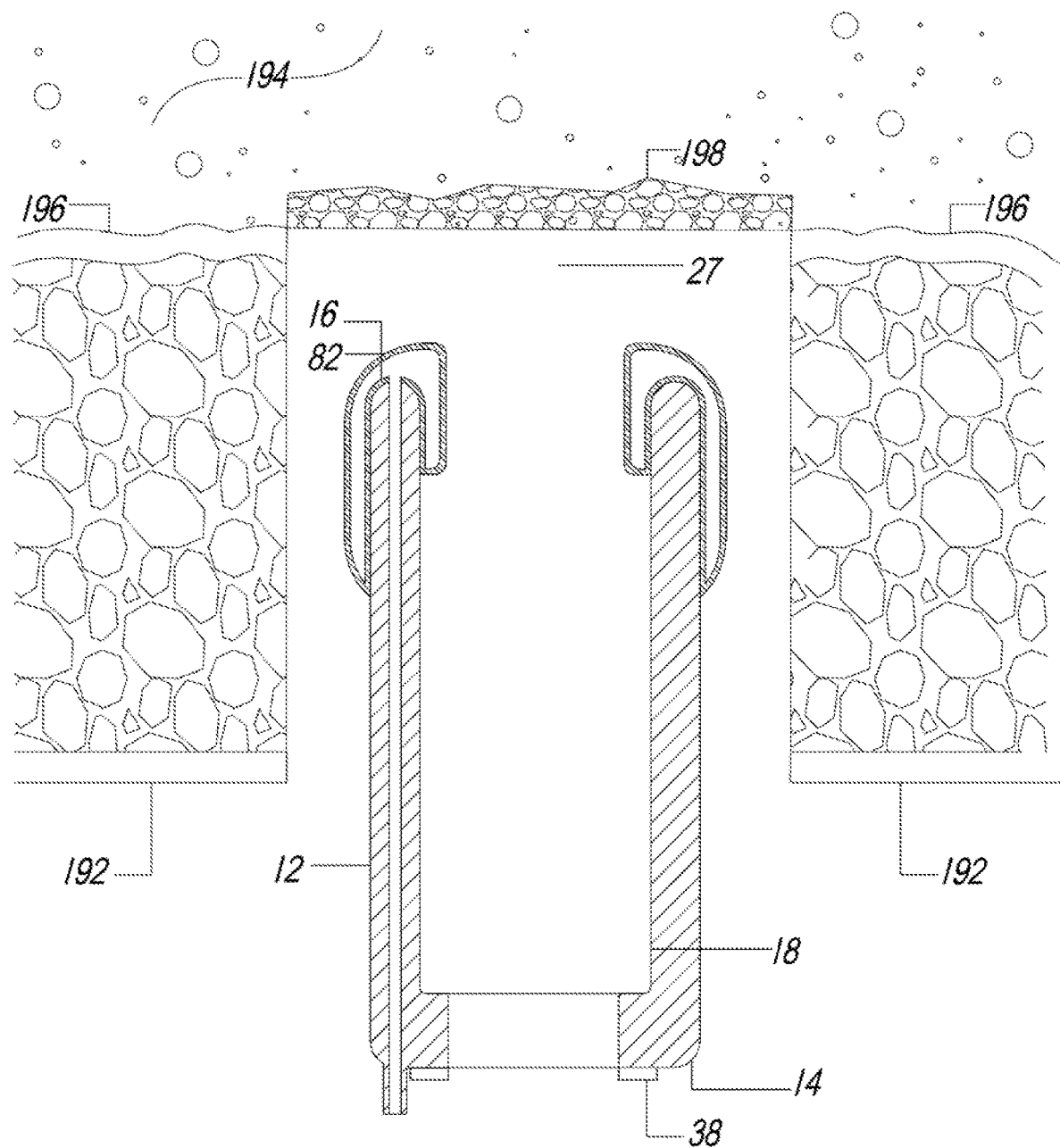
FIG. 19 is a schematic sectional representation of the embodiment of FIG. 13 in use showing an occlusion balloon deflated to assess the stability of a hemostatic layer that has formed at a puncture site.
Figure 20:
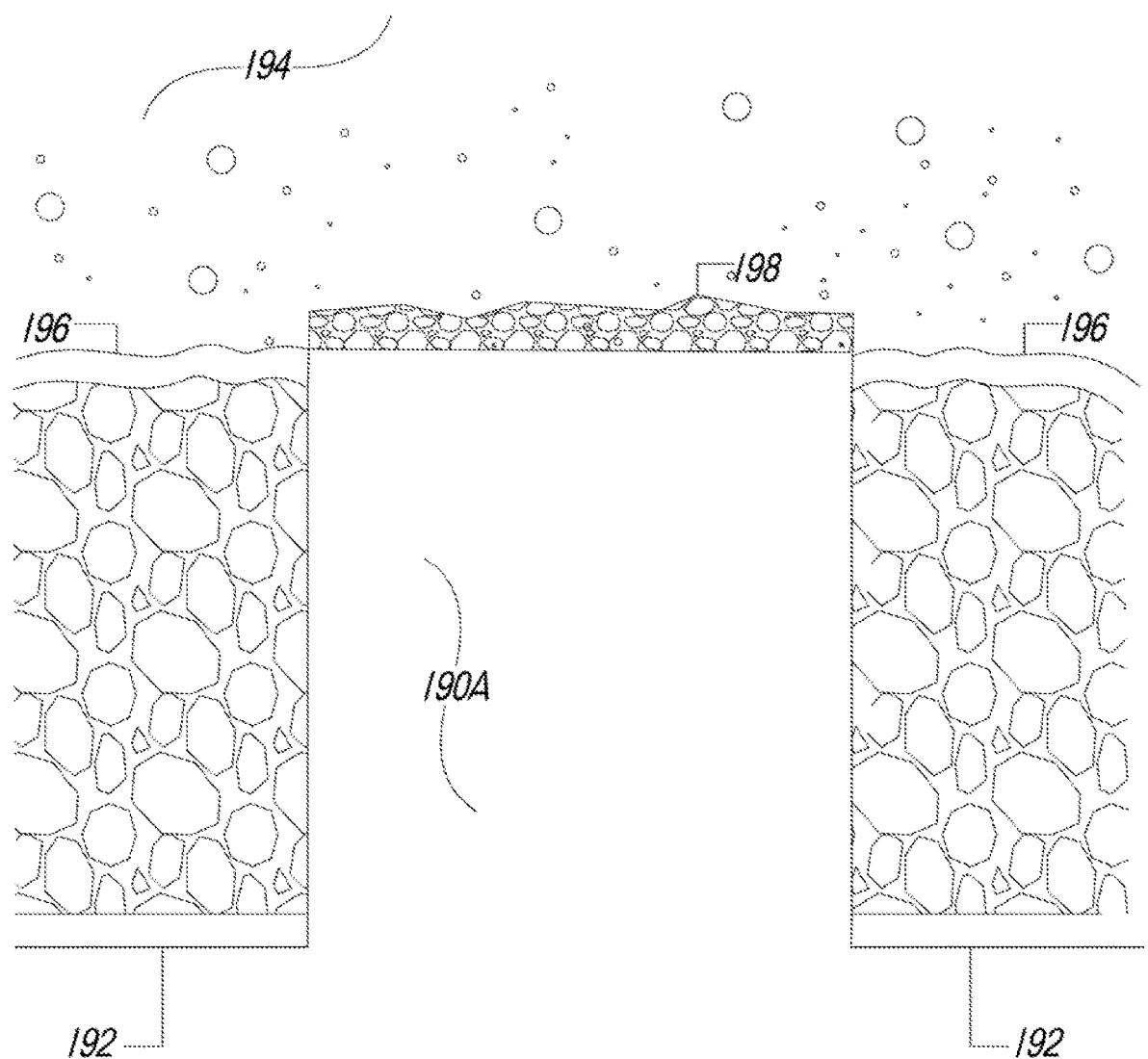
FIG. 20 is a schematic sectional representation of hemostasis confirmed after a balloon closure device has been removed, leaving behind a hemostatic plug.
Figure 21A:
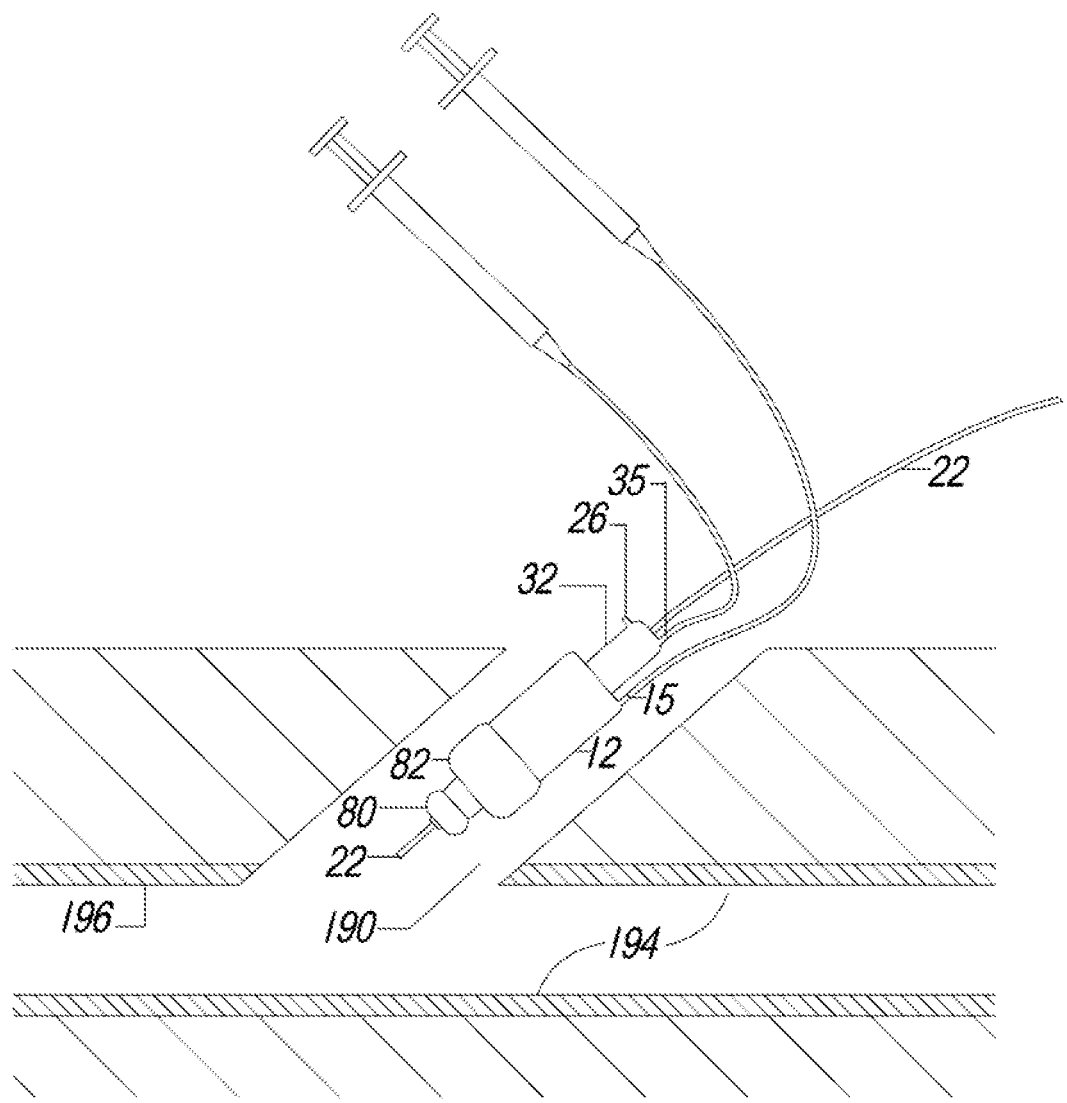
FIG. 21A is a partially sectional side view of a percutaneous puncture communicating with a blood vessel showing a step of a method for sealing the puncture, in accordance with the present invention.
Figure 21B:
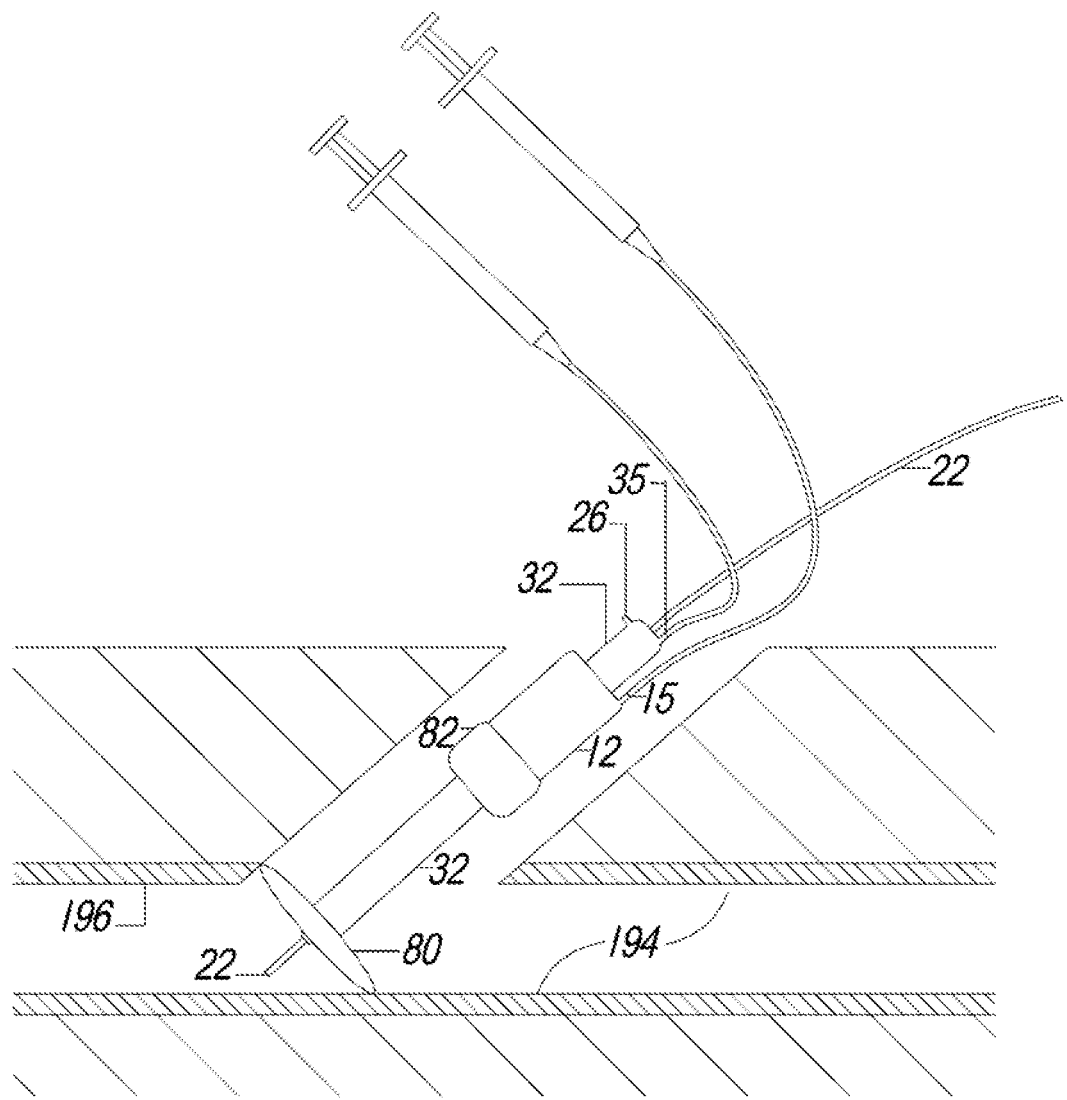
FIG. 21B is a partially sectional side view of a step subsequent to the step shown in FIG. 21A.
Figure 21C:
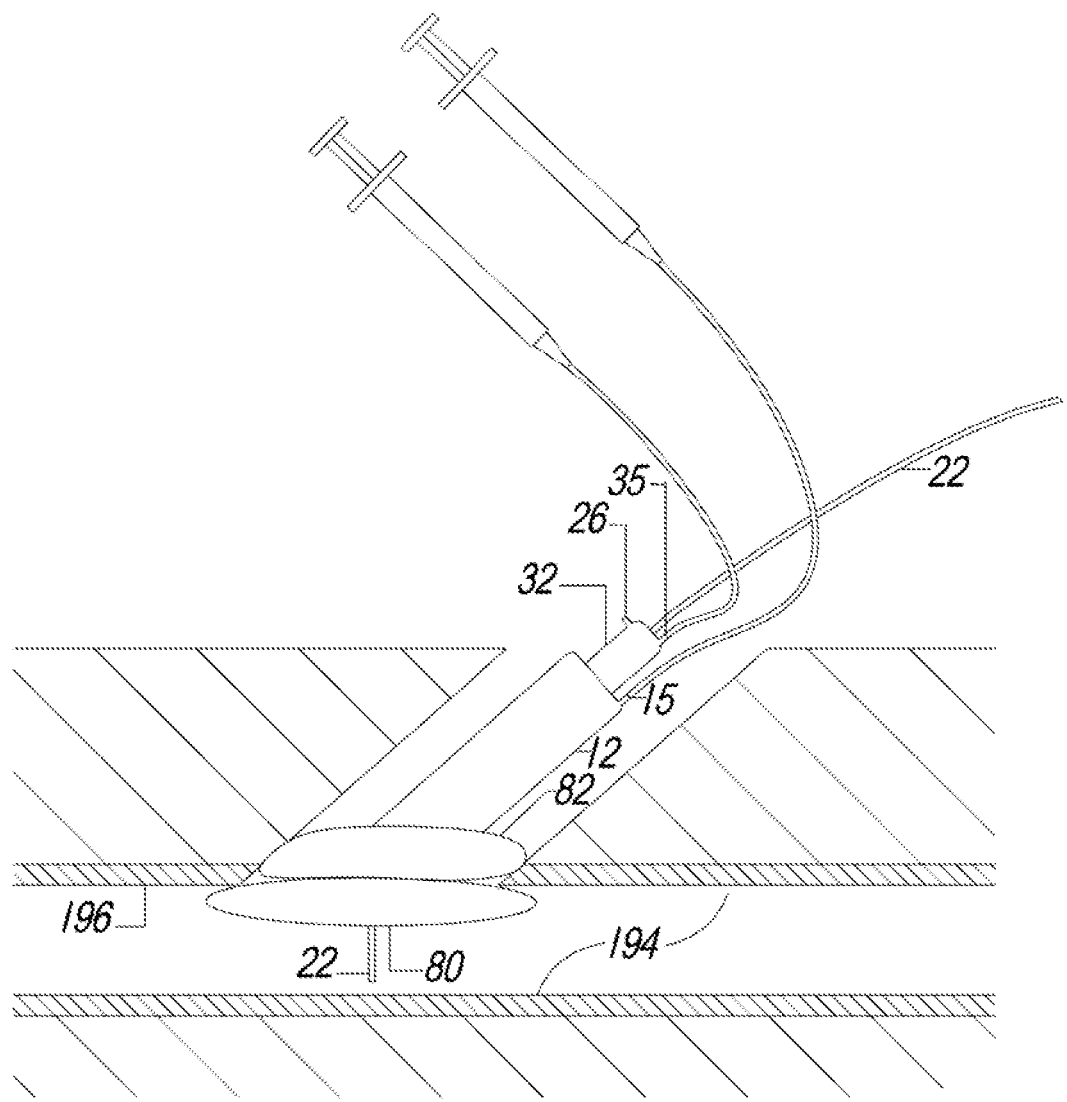
FIG. 21C is a partially sectional side view of a step subsequent to the step shown in FIG. 21B.
Figure 21D:
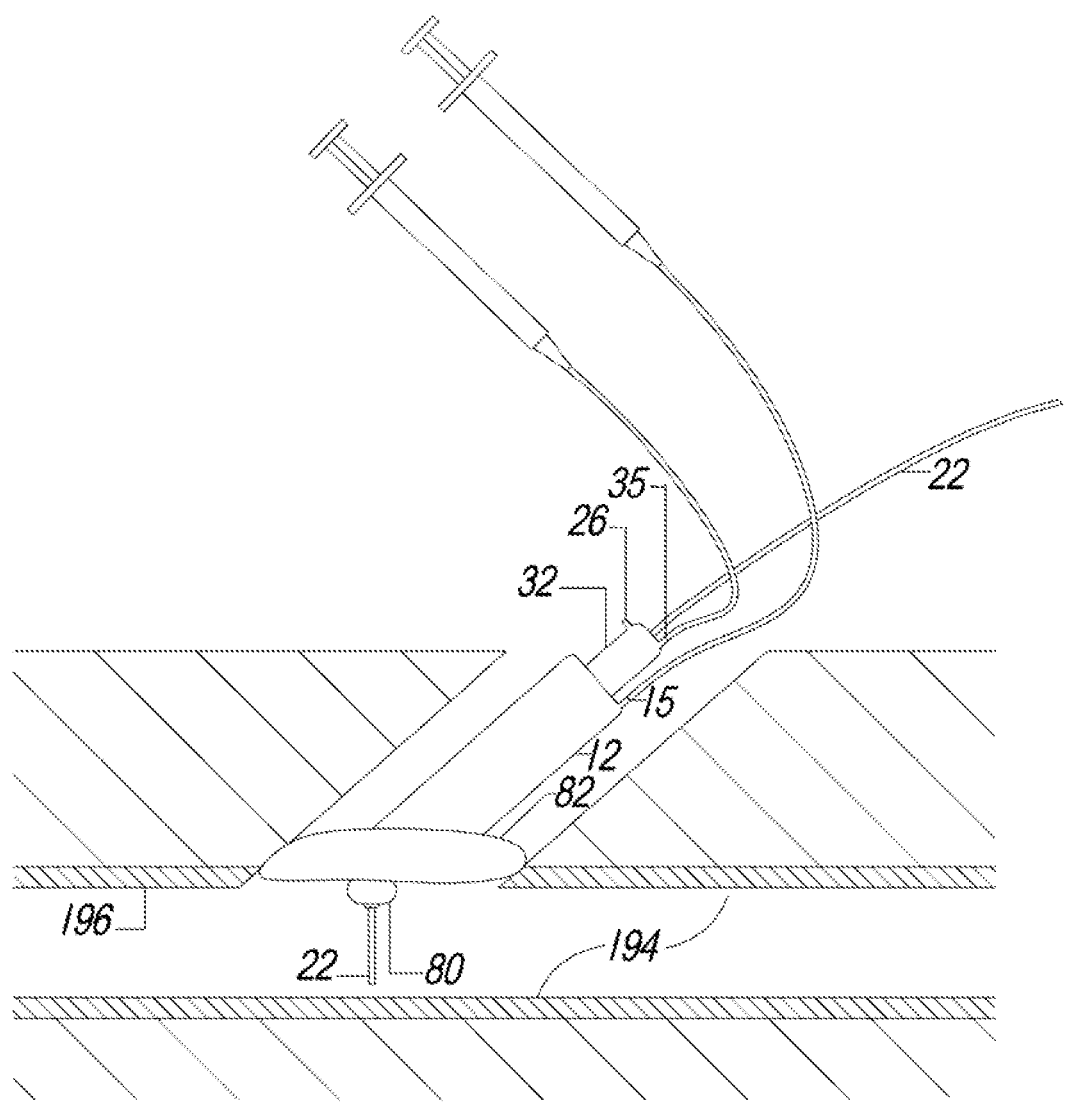
FIG. 21D is a partially sectional side view of a step subsequent to the step shown in FIG. 21C.
Figure 21E:
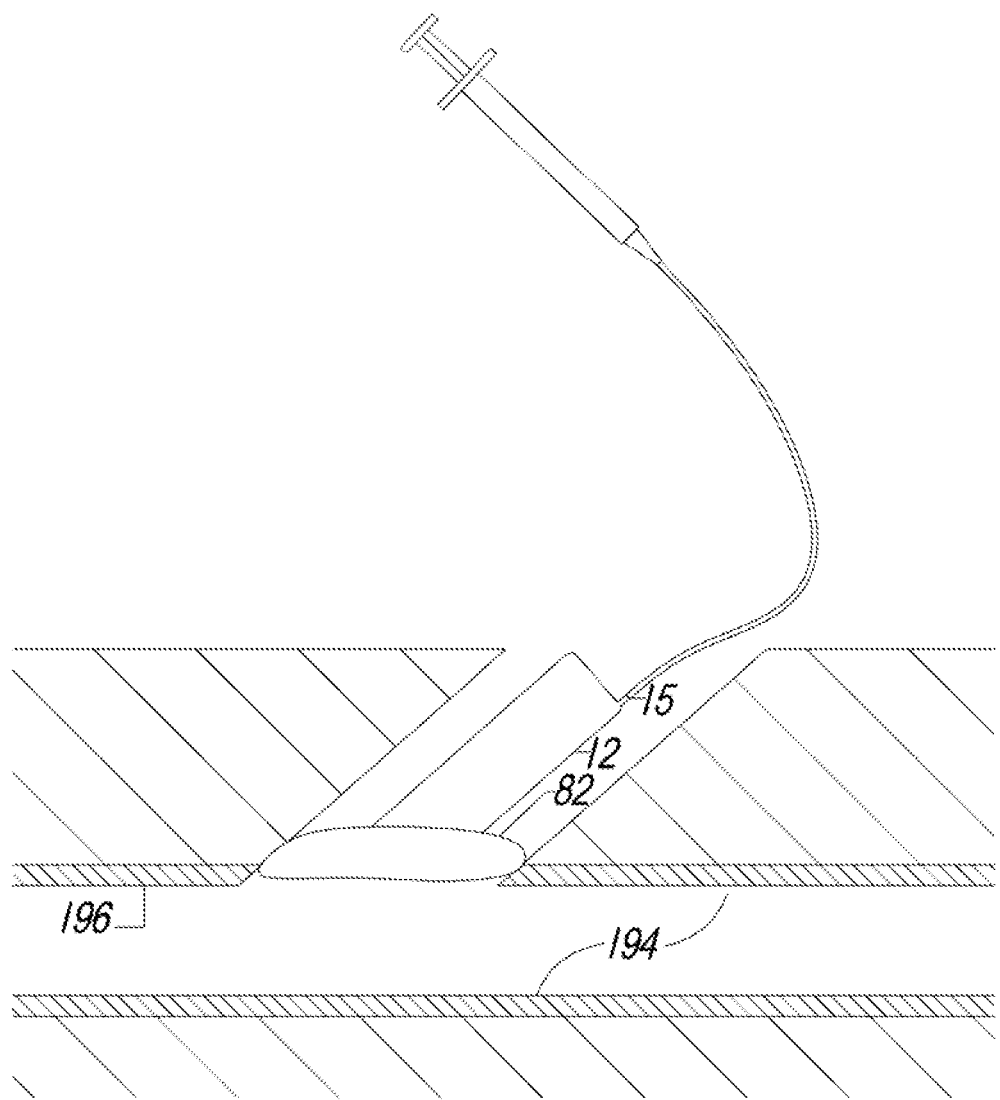
FIG. 21E is a partially sectional side view of a step subsequent to the step shown in FIG. 21D.
Figure 21F:
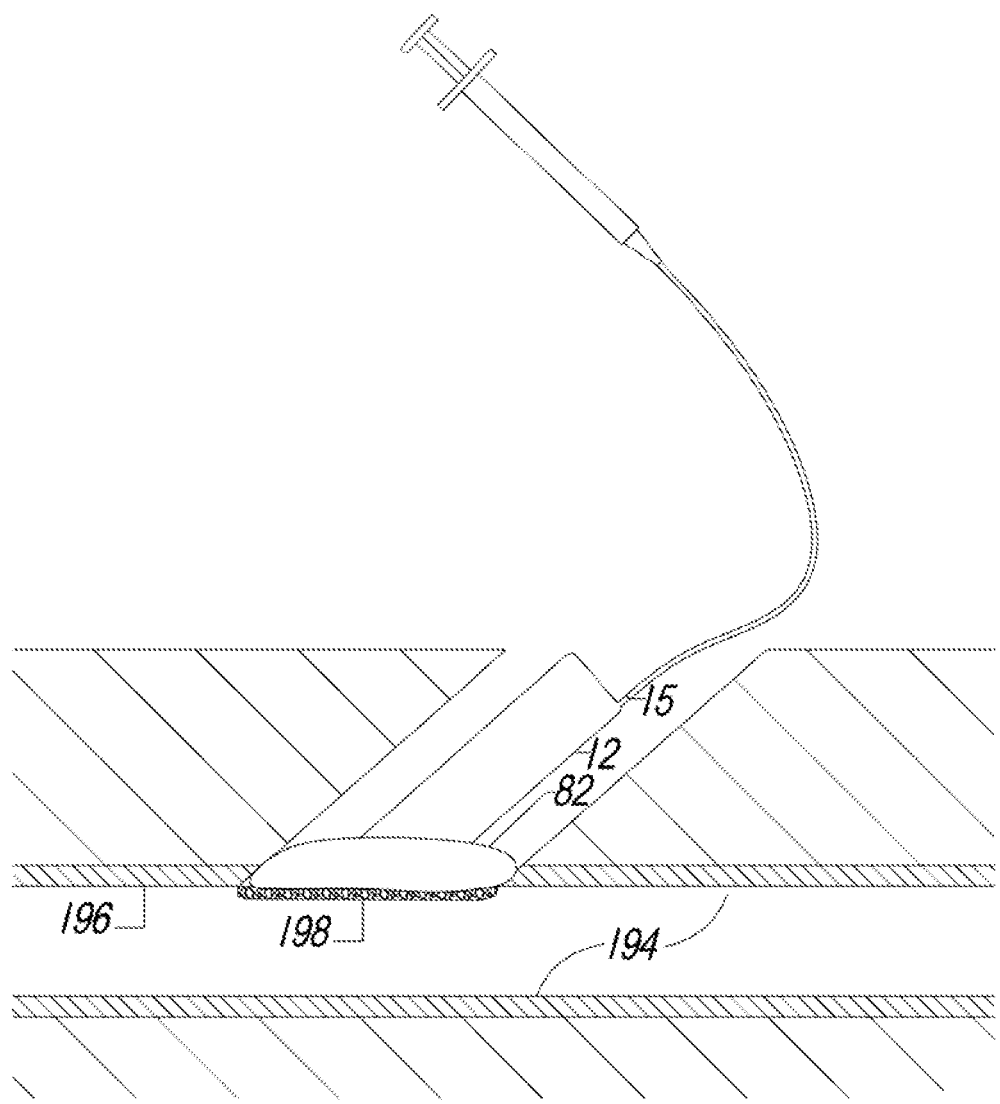
FIG. 21F is a partially sectional side view of a step subsequent to the step shown in FIG. 21E.
Figure 21G:
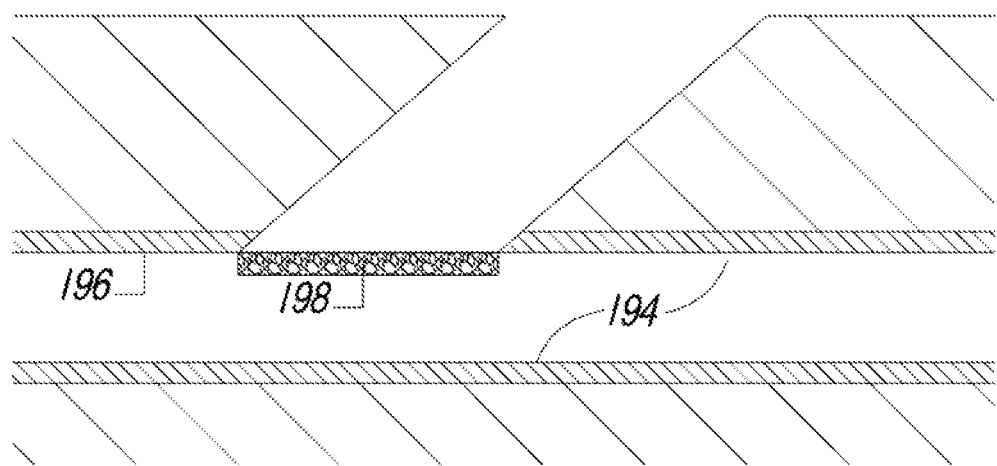
FIG. 21G is a partially sectional side view of a step subsequent to the step shown in FIG. 21F.

FIGS. 13-20 demonstrate another embodiment that may result in a smaller profile balloon closure device. In this embodiment, a low profile dilator/introducer 52 is used instead of the anchor catheter. Such a dilator/introducer 52 may similarly have a distal vessel locator 28 to indicate entry into the blood vessel lumen, but would lack an anchor balloon. Instead, the guide wire may be removed and a simple balloon catheter 62, as is known in the art, may be advanced through the guide wire lumen, enter the blood vessel and function similarly to the anchor balloon. As shown in FIG. 14, the balloon 84 may be inflated through lumen 45 and pulled back along with the dilator/introducer 52, to maintain the balloon 84 substantially against the puncture 190. The subsequent steps demonstrated in FIGS. 15-20 are substantially similar to those previously demonstrated in FIGS. 6-12, and described previously.

As may be appreciated by the description above, deployment of the balloon closure device is easy, quick, reliable, and should avoid significant discomfort to the patient. Hemostasis occurs almost instantaneously, e.g., in 15 seconds or less, when the closure device is deployed properly.

Should there be any residual bleeding from the puncture tract or arterial lumen, external pressure may be applied, e.g., by pressing manually against the skin 192 overlying the arterial lumen 194. External pressure may be maintained for sufficient time to allow substantial sealing of any residual bleeding remaining upon removing the balloon closure device 10.

As should be appreciated from the foregoing, the closure device, and its method of use, as shown in FIGS. 21A through 21G, enables the ready, effective and efficient sealing of a percutaneous puncture in an artery (or vein). Thus, it is expected that the balloon closure device 10 will be a significant advancement in the fields of cardiology and radiology. The device may allow continuance of anticoagulation post-procedure, more aggressive use of thrombolytic agents and safer use of large bore catheters. It should also reduce discomfort and complication rates for patients. It may allow early or even immediate ambulation with the device "locked" in place. It may allow many in-patient procedures to be performed safely on an out-patient basis, decrease the time and cost of interventional procedures, and reduce exposure of hospital personnel to human blood.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A system for causing hemostasis at a puncture and a puncture tract, the system comprising:
    an inner member comprising an expandable member at an inner member distal end and an inflation lumen that extends from an inner member proximal end to an interior of the expandable member, wherein the inner member further comprises a vessel locator comprising a lumen extending from one or more vessel locator distal holes to a vessel locator proximal hole; and
    an outer member comprising a lumen sized and shaped to allow the inner member to slide therein, an occlusion balloon at an outer member distal end, and an inflation lumen that extends from an outer member proximal end to the interior of the occlusion balloon,
    wherein the expandable member can be inflated by fluid flowing through the inner member inflation lumen so that the expandable member can inflate in a subcutaneous vessel of a living being, and wherein the occlusion balloon can be inflated by fluid flowing through the outer member inflation lumen so that the occlusion balloon can enable the occlusion of a puncture and contact and apply pressure to a puncture tract extending from the skin of the living being to the puncture.

2. A system according to claim 1 wherein the vessel locator allows for back-bleeding from the vessel to provide a perceptible signal indicative of the location of the inner member with respect to the vessel.

3. A system according to claim 1 wherein the inner member comprises a guidewire lumen.

4. A system according to claim 1 wherein the system comprises a hub connector that biases the inner member relative to the outer member.

5. A system according to claim 1 wherein the inner member is an anchor catheter.

6. A system according to claim 1 wherein the outer member is an occlusion catheter.

7. A system according to claim 1 wherein the inner member is a dilator.

8. A system according to claim 1 wherein the inner member is a balloon catheter.

9. A system according to claim 1 wherein the inner member is removeable from the outer member while the occlusion balloon is inflated and wherein the occlusion balloon can then enable the occlusion of the puncture.

10. A system according to claim 1 wherein the occlusion balloon is coated with a procoagulant material to enhance coagulation and hemostasis.

11. A system according to claim 1 wherein the occlusion balloon can close the puncture.

12. A system according to claim 1 wherein the one or more vessel locator distal holes are positioned on the inner member proximal to the expandable member.

13. A system for causing hemostasis at a puncture in a vessel, the system comprising:
    an inner member comprising a vessel locator comprising a lumen extending from one or more vessel locator distal holes to a vessel locator proximal hole; and
    an outer member comprising a lumen sized and shaped to allow the inner member to slide therein, an occlusion balloon at an outer member distal end, and an inflation lumen that extends from an outer member proximal end to the interior of the occlusion balloon,
    wherein the inner member can be positioned within a vessel having a puncture, wherein the position of the inner member within the vessel can be determined by back-bleeding from the vessel through the vessel locator to provide a perceptible signal indicative of the location of the inner member with respect to the vessel, and wherein the occlusion balloon can be inflated by fluid flowing through the outer member inflation lumen so that the occlusion balloon can enable the occlusion of the puncture.

14. A system according to claim 13 wherein the occlusion balloon can be inflated to also contact and apply pressure to a puncture tract extending from the skin of the living being to the puncture.

15. A system according to claim 13 wherein the inner member comprises a guidewire lumen.

16. A system according to claim 13 wherein the system comprises a hub connector that biases the inner member relative to the outer member.

17. A system according to claim 13 wherein the inner member is removeable from the outer member while the occlusion balloon is inflated and wherein the occlusion balloon can then enable the occlusion of the puncture.

18. A system according to claim 13 wherein the occlusion balloon can close the puncture.

19. A system for causing hemostasis at a puncture and a puncture tract, the system comprising:

an inner member, the inner member being positionable within a vessel having a puncture; and an outer member comprising a lumen sized and shaped to allow the inner member to slide therein, an occlusion balloon at an outer member distal end, and an inflation lumen that extends from an outer member proximal end to the interior of the occlusion balloon, wherein the occlusion balloon is attached to the exterior of the outer member at a position proximal to the distal end of the outer member, and wherein the occlusion balloon can be inflated by fluid flowing through the outer member inflation lumen so that the occlusion balloon can enable the occlusion of the puncture and can contact and apply pressure to a puncture tract extending from the skin of the living being to the puncture.

20. A system according to claim 19 wherein the inner member comprises a vessel locator comprising a lumen extending from one or more vessel locator distal holes to a vessel locator proximal hole, wherein the vessel locator can provide a perceptible signal indicative of the location of the inner member with respect to the vessel.

21. A system according to claim 19 wherein the inner member comprises a guidewire lumen.

22. A system according to claim 19 wherein the occlusion balloon can close the puncture.

23. A system according to claim 19 wherein the occlusion balloon is also attached to the distal end of the outer member.

* * * * *